US008709809B2

(12) United States Patent
Wen et al.

(10) Patent No.: US 8,709,809 B2
(45) Date of Patent: Apr. 29, 2014

(54) NANOFIBERS CONTAINING LATENT REACTIVE GROUPS

(75) Inventors: Jie Wen, Eden Prairie, MN (US); Patrick E. Guire, Hopkins, MN (US)

(73) Assignee: Innovative Surface Technologies, Inc., St. Paul, MN (US)

( * ) Notice: Subject to any disclaimer, the term of this patent is extended or adjusted under 35 U.S.C. 154(b) by 182 days.

(21) Appl. No.: 12/666,173

(22) PCT Filed: Jun. 20, 2008

(86) PCT No.: PCT/US2008/067739
§ 371 (c)(1),
(2), (4) Date: Sep. 29, 2010

(87) PCT Pub. No.: WO2009/002869
PCT Pub. Date: Dec. 31, 2008

(65) Prior Publication Data
US 2011/0020917 A1    Jan. 27, 2011

Related U.S. Application Data

(60) Provisional application No. 60/945,807, filed on Jun. 22, 2007.

(51) Int. Cl.
*C12M 1/00*     (2006.01)
*A61L 27/34*    (2006.01)

(52) U.S. Cl.
USPC ............ 435/398; 435/395; 435/369; 435/399

(58) Field of Classification Search
USPC .......................................... 435/396, 398, 399
See application file for complete search history.

(56) References Cited

U.S. PATENT DOCUMENTS

| 3,580,927 | A | 5/1971 | Wear |
| 3,959,078 | A | 5/1976 | Guire |
| 4,043,331 | A | 8/1977 | Martin et al. |
| 4,266,055 | A | 5/1981 | Inoue et al. |
| 4,605,413 | A | 8/1986 | Urry et al. |
| 4,722,906 | A | 2/1988 | Guire |
| 4,973,493 | A | 11/1990 | Guire |
| 5,002,582 | A | 3/1991 | Guire et al. |
| 5,202,361 | A | 4/1993 | Zimmerman et al. |
| 5,258,041 | A | 11/1993 | Guire et al. |
| 5,331,027 | A | 7/1994 | Whitbourne |
| 5,414,075 | A | 5/1995 | Swan et al. |
| 5,522,879 | A | 6/1996 | Scopelianos |
| 5,563,056 | A | 10/1996 | Swan et al. |
| 5,637,460 | A | 6/1997 | Swan et al. |
| 5,714,360 | A | 2/1998 | Swan et al. |
| 5,942,555 | A | 8/1999 | Swanson et al. |
| 6,077,698 | A | 6/2000 | Swan et al. |
| 6,096,369 | A | 8/2000 | Anders et al. |
| 6,278,018 | B1 | 8/2001 | Swan et al. |
| 6,391,948 | B1 | 5/2002 | Clark et al. |
| 6,395,429 | B1 | 5/2002 | Kang et al. |
| 7,348,055 | B2 | 3/2008 | Chappa et al. |
| 2002/0004140 | A1 | 1/2002 | Swan et al. |
| 2003/0165613 | A1 | 9/2003 | Chappa et al. |
| 2005/0095695 | A1 | 5/2005 | Shindler et al. |
| 2006/0030669 | A1 | 2/2006 | Taton et al. |
| 2007/0003707 | A1 | 1/2007 | Guire et al. |
| 2007/0082393 | A1 * | 4/2007 | Lodhi et al. ................... 435/325 |
| 2008/0021126 | A1 | 1/2008 | Dietliker et al. |

FOREIGN PATENT DOCUMENTS

| EP | 1857126 A1 | 11/2007 |
| JP | 57042742 | 3/1982 |
| JP | 57117564 | 7/1982 |
| JP | 59043061 | 3/1984 |
| WO | 93/16131 | 8/1993 |
| WO | WO 93/16176 | 8/1993 |
| WO | WO 97/07161 | 2/1997 |
| WO | 98/03489 | 1/1998 |
| WO | WO 01/26702 A | 4/2001 |
| WO | 01/40367 | 6/2001 |
| WO | 03/025267 | 3/2003 |
| WO | WO 03/097117 A1 | 11/2003 |
| WO | WO 2004/044281 A2 | 5/2004 |

(Continued)

OTHER PUBLICATIONS

Kavanagh et al.; Poly(N-isopropylacrylamide) copolymer films as vehicles for the sustained delivery of proteins to vascular endothelial cells; Journal of Biomedical Materials Research Part A; vol. 72A, No. 1, pp. 25-35, published Jan. 1, 2005.*
Chen et al.; Ultrafine Hydrogel Fibers with Dual Temperature- and pH-Responsive Swelling Behaviors; Journal of Polymer Science: Part A: Polymer Chemistry, vol. 42, pp. 6331-6339 (2004).*
International Search Report for corresponding International Patent Application No. PCT/US2008/067739, completed Apr. 29, 2009, 7 pages.
Allen, N. et al., Photochemistry and Photopolymerization Activity of Novel 4-Alkylamino Benzophenone Initiators, Eur. Polym. J.(26), p. 1345-1353 (1990).

(Continued)

*Primary Examiner* — Michele K Joike
*Assistant Examiner* — Antonio Galisteo Gonzalez
(74) *Attorney, Agent, or Firm* — Weaver Legal and Consulting LLC

(57) ABSTRACT

A nanofiber is formed by combining one or more natural or synthetic polymeric materials and one or more than one cross-linking agents having at least two latent reactive activatable groups. The latent reactive activatable nanofiber may be used to modify the surface of a substrate by activating at least one of the latent reactive activatable groups to bond the nanofiber to the surface by the formation of a covalent bond between the surface of the substrate and the latent reactive activatable group. Some of the remaining latent reactive activatable group(s) are left accessible on the surface of the substrate, and may be used for further surface modification of the substrate. Biologically active materials may be immobilized on the nanofiber modified surface by reacting with the latent reactive groups that are accessible on the surface of the substrate.

17 Claims, 5 Drawing Sheets

(56) References Cited

FOREIGN PATENT DOCUMENTS

| WO | WO 2006135910 A1 | * | 12/2006 |
|----|------------------|---|---------|
| WO | WO 2007/012050 A2 |  | 1/2007 |
| WO | WO 2007/144356 A1 |  | 12/2007 |
| WO | WO 2009/002858 |  | 12/2008 |

OTHER PUBLICATIONS

Blawas, A.S., et al., Review: Protein Patterning, Biomaterials(19), p. 595-609 (1998).

Cao, X., et al., Photoimmobilization of biomolecules within a 3-dimensional hydrogel matrix, J. Biomater. Sci. Polymer Edn.(13), p. 623-636 (2002).

Chen, H., et al., Ultrafine Hydrogel Fibers with Dual Temperature- and pH-Responsive Swelling Behaviors, J. of Pol. Sci. A: Pol. Chem. (42) p. 6331-6339 (2004).

Chua, K-N., et al., Stable immobilization of rat hepatocyte spheroids on galactosylated nanofiber scaffold, Biomaterials(26), p. 2537-2547 (2005).

Fang, J., et al., Applications of electrospun nanofibers, Chinese Science Bulletin(53), p. 2265-2286 (2008).

Geismann, C., et al, Photoreactive Functionalization of Poly(ethylene terephthalate) Track-Etched Pore Surf. w/ "Smart" Polym Sys, Macromol. Chem. Phys.(206), p. 268-281 (2005).

Jin, Y., et al., Photocrosslinked Electrospun Chitosan-Based Biocompatible Nanofibers, J. of Applied Pol. Sci.(109), p. 3337-3343 (2008).

Kim, DJ, et al, Formation of Thermoresponsive Poly(N-isopropylacrylamide)/Dextran Particles by Atom Transfer Radical Polymerization, Macromol. Rapid Comm(24), p. 517-521 (2003).

Kim, S.H., et al., Reactive Electrospinning of Cross-Linked Poly(2-hydroxyethyl methacrylate) Nanofibers and Elastic . . . , Macromolecules (38), p. 3719-3723 (2005).

Ko, Y-G., et al., Development of Rapid Cell Recovery System Using Temperature-Responsive Nanofiber Surfaces, Key Engineering Materials (342-343), p. 249-252 (2007).

Kroschwitz, ed., Plastics, Concise Encyclopedia of Polymer Science and Engineering, John Wiley & Sons, 1990, pp. 462-464.

Kubota, H., et al., Photografting of Acrylamide on Ethylene-Vinyl Alcohol Copolymer Film, Polymer International(34), p. 313-317 (1994).

Li, D., et al., Electrospinning of Nanofibers: Reinventing the Wheel?, Adv. Mater.(16), p. 1151-1170 (2004).

Liu, H. et al., Ionic-Strength- and pH-Responsive Poly[acrylamied-co(maleic acid)] Hydrogel Nanofibers, Macromol. Chem. Phys. (208), p. 874-880 (2007).

Ma, Z., et al., Potential of Nanofiber Matrix as Tissue-Engineering Scaffolds, Tissue Engineering(11), p. 101-109 (2005).

Ma, Z., et al, Surface engineering of electrospun polyethylene terephthalate (PET) nanofibers towards development of a new material . . . , Biomaterials(26), p. 2527-36 (2005).

Mark, S, et al, Bioconjugation of Alk. Phosphatase to Mechanically Processed, Aq. Suspendible Electrospun Polym Nanofibers for Use . . . , Marcomol. Biosci.(8), p. 484-498 (2008).

Min, B.M. et al., Electrospinning of silk fibroin nanofibers and its effect on the adhesion and spreading of normal human keratinocytes . . . , Biomaterials(25), p. 1289-97 (2004).

Okuzaki, H., et al., Thermo-Responsive Nanofiber Mats, Macromolecules(42), p. 5916-5918 (2009).

Ramakrishna, S., et al., Electrospun nanofibers: solving global issues, Materials Today(9), p. 40-50 (2006).

Rothenberg, et al, Human and Rat Hepatocytes Cultured on Ultra-WebTM and Ultra-Web Polyamine Synth. Matrices show Enhanced Physiologic Activity, Application Note (4 pgs, 2008).

Rothenberg, M, et al, Rat Hepatocyte Culture Physiology Shows Enhanced Cytochrome P450 Activity on a Synthetic Extracellular Matrix, Cell Notes(20), p. 18-20 (2008).

Ryadnov, M.G., et al., Fiber Recruiting Peptides: Noncovalent Eecoration of an Engineered Protein Scaffold, J. Am. Chem. Soc. (126), p. 7454-7455 (2004).

Sanders, J. et al., Fibro-porous meshes made from polyurethane micro-fibers: effects of surface charge on tissue response, Biomaterials (26), p. 813-818 (2005).

Shengguag, C. et al., Synth. of pH-resp. crosslinked poly[styrene-co(maleic sodium anhydride)] and cellulose comp. hydrogel nanofibers . . . , Polym. Int(58) p. 545-551 (2009).

Ulbrict, M. et al, Ultrafiltration membrane surfaces with grafted polymer 'tentacles': prep, char. and app. for covalent protein bonding, Biomaterials (19), p. 1229-37 (1998).

Yu, J., et al., Photocrosslinked Electrospun Chitosan-Based Biocompatible Nanofibers, J. of Applied Polym. Sci.,(109), p. 3337-3343 (2008).

Hungarian Intellectual Property Office Search Report, provided to the Intellectual Property Office of Singapore for corresponding Singapore Patent Application No. 200908551-5, mailed Feb. 15, 2011 (7 pages).

* cited by examiner

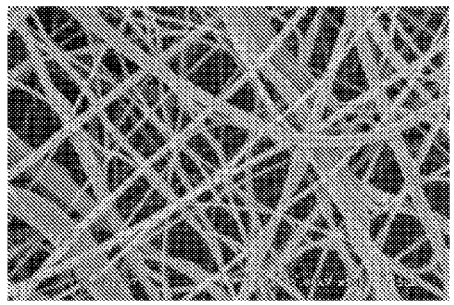
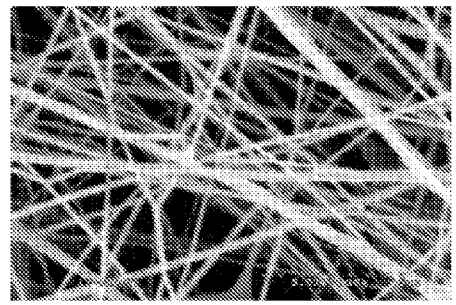
Fig. 1A            Fig. 1B
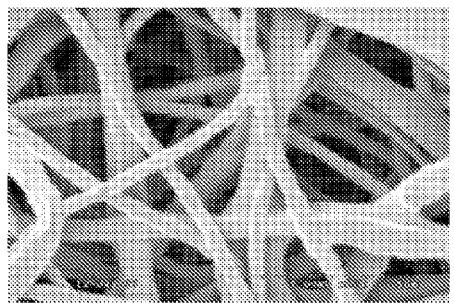
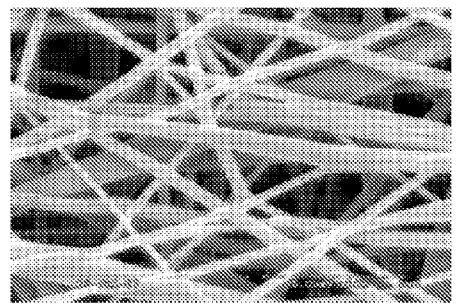
Fig. 1C            Fig. 1D
SEM images of photoreactive PCL nanofibers. A) 0%; B) 1%; C) 5%; D) 10%; scale bar 5 μm; average diameter of a minimum of 20 fibers at different points ± SD.

Carboxy group densities on 0, 5 and 10% nanofibers created by PAA deposition

Amine group densities on 0, 5, and 10% nanofibers created by (80:20) DMA/APMA deposition and graft polymerization of APMA Carboxy group densities on 1% nanofibers through different surface modifications Immobilization of HRP on various 1% nanofiber surfaces HRP activity on various 1% nanofiber surfaces Enzymatic degradation of photocrosslinked nanofibers SEM images of enzymatically degraded photocrosslinked nanofibers.
A) 0%; B) 1%; C) 5%; D) 10%; scale bar 5 μm

NANOFIBERS CONTAINING LATENT REACTIVE GROUPS

This invention was made with government support under Grant No. 1R43EB005905-01, awarded by the National Institutes of Health. The government has certain rights in the invention.

TECHNICAL FIELD

The present invention generally relates to nanofibers and nanofiber modified surfaces. More particularly, the present invention is directed to nanofibers including one or more multi-functional cross-linking agents each having at least two latent reactive activatable groups. The nanofibers containing latent reactive activatable cross-linking agents may be used to modify a surface of a substrate.

BACKGROUND

Nanofibers are being considered for a variety of applications because of their unique properties including high surface area, small fiber diameter, layer thinness, high permeability, and low basis weight. More attention has been focused on functionalized nanofibers having the capability of incorporating active chemistry, especially in biomedical applications such as wound dressing, biosensors and scaffolds for tissue engineering.

Nanofibers may be fabricated by electrostatic spinning (also referred to as electrospinning). The technique of electrospinning of liquids and/or solutions capable of forming fibers, is well known and has been described in a number of patents, such as, for example, U.S. Pat. Nos. 4,043,331 and 5,522,879. The process of electrospinning generally involves the introduction of a liquid into an electric field, so that the liquid is caused to produce fibers. These fibers are generally drawn to a conductor at an attractive electrical potential for collection. During the conversion of the liquid into fibers, the fibers harden and/or dry. This hardening and/or drying may be caused by cooling of the liquid, i.e., where the liquid is normally a solid at room temperature; by evaporation of a solvent, e.g., by dehydration (physically induced hardening); or by a curing mechanism (chemically induced hardening).

The process of electrostatic spinning has typically been directed toward the use of the fibers to create a mat or other non-woven material, as disclosed, for example, in U.S. Pat. No. 4,043,331. Nanofibers ranging from 50 nm to 5 µm in diameter can be electrospun into a nonwoven or an aligned nanofiber mesh. Due to the small fiber diameters, electrospun textiles inherently possess a very high surface area and a small pore size. These properties make electrospun fabrics potential candidates for a number of applications including: membranes, tissue scaffolding, and other biomedical applications. Recently, efforts have focused on using electrospinning techniques to produce nonwoven membranes of nanofibers.

Nanofibers can be used to modify the surface of a substrate. Most nanofiber surfaces have to be engineered to obtain the ability to immobilize biomolecules. Surface modification of synthetic biomaterials, with the intent to improve biocompatibility, has been extensively studied, and many common techniques have been considered for polymer nanofiber modification. For example, Sanders et al. in "Fibro-Porous Meshes Made from Polyurethane Micro-Fibers: Effects of Surface Charge on Tissue Response" *Biomaterials* 26, 813-818 (2005) introduced different surface charges on electrospun polyurethane (PU) fiber surfaces through plasma-induced surface polymerization of negatively or positively charged monomers. The surface charged PU fiber mesh was implanted in rat subcutaneous dorsum for 5 weeks to evaluate tissue compatibility, and it was found that negatively charged surfaces may facilitate vessel ingrowth into the fibroporous mesh biomaterials. Ma et al. in "Surface Engineering of Electrospun Polyethylene Terephthalate (PET) Nanofibers Towards Development of a New Material for Blood Vessel Engineering" *Biomaterials* 26, 2527-2536 (2005) conjugated gelatin onto formaldehyde pretreated polyethylene teraphthalate (PET) nanofibers through a grafted polymethacrylic acid spacer and found that the gelatin modification improved the spreading and proliferation of endothelial cells (ECs) on the PET nanofibers, and also preserved the EC's phenotype. Chua et al. in "Stable Immobilization of Rat Hepatocyte Spheroids on Galactosylated Nanofiber Scaffold" *Biomaterials* 26, 2537-2547 (2005) introduced galactose ligand onto poly(e-caprolactone-co-ethyl ethylene phosphate) (PCLEEP) nanofiber scaffold via covalent conjugation to a poly(acrylic acid) spacer UV-grafted onto the fiber surface. Hepatocyte attachment, ammonia metabolism, albumin secretion and cytochrome P450 enzymatic activity were investigated on the 3-D galactosylated PCLEEP nanofiber scaffold as well as the functional 2-D film substrate.

SUMMARY

The methods and techniques summarized above are costly, complicated, or material specific. Thus, there is a need for a surface modification approach that is more general and easy to use and can be applied under mild conditions to a wide variety of nanofibers.

According to one embodiment of the present invention, a nanofiber includes one or more natural or synthetic polymeric materials and one or more cross-linking agents each having at least two latent reactive activatable groups. In use, photochemically or thermally latent reactive groups will form covalent bonds when subjected to a source of energy. Suitable energy sources include radiation and thermally energy. In some embodiments, the radiation energy is visible, ultraviolet, infrared, x-ray or microwave electromagnetic radiation.

The cross-linking agent may have at least two latent reactive activatable groups. These latent reactive groups may be the same or may be different. For example, all of the latent reactive groups may be photochemically reactive groups. Alternatively, in other embodiments of the invention the cross-linking agent may include both photochemically and thermally reactive groups. Further, the cross-linking agent may be monomeric or polymeric materials or may be a mixture of both monomeric and polymeric materials.

According to various embodiments of the present invention, the polymeric material of the nanofiber may be hydrophilic, hydrophobic, amphiphilic or thermally responsive, depending on the desired application. According to yet a further embodiment of the present invention, the nanofiber also may be either biodegradable or non-biodegradable polymers. In still further embodiments the nanofiber may include a biologically active material.

The nanofiber typically has a diameter ranging from 1 nm to 100 microns and may have a diameter ranging from 1 nm to 1000 nm. The nanofiber may have an aspect ratio in a range of about at least 10 to at least 100.

According to another embodiment of the present invention, a latent reactive activatable nanofiber is produced by combining one or more polymeric materials with one or more cross-linking agents each having at least two latent reactive activatable groups and forming at least one nanofiber from the combination. The nanofiber may be formed by electrospinning the combination containing the polymeric materials and the cross-linking agent. According to yet a further embodiment of the present invention, the combination may also include biologically active materials or be further combined with a functional polymer that will subsequently react with biologically active materials. Functional polymers include any suitable polymer having one or more functional groups that will react with a biologically active material. Representative functional groups for these polymers include carboxy, ester, epoxy, hydroxyl, amido, amino, thio, N-hydroxy succinimide, isocyanate, anhydride, azide, aldehyde, cyanuryl chloride or phosphine groups.

According to yet another embodiment, the present invention provides method of coating a surface of a substrate. According to one embodiment of the present invention, the method includes combining one or more polymeric materials and one or more cross-linking agents each having at least two latent reactive activatable groups, forming at least one nanofiber from the combination, contacting the surface of the substrate with the nanofiber; and forming a bond between the nanofiber and the surface. According to a further embodiment of the present invention, the method includes activating at least one of the latent reactive activatable groups with a source of energy to bond the nanofiber to a biologically active material. According to an alternative embodiment of the present invention, the method includes simultaneously activating a first latent reactive activatable group to bond the nanofiber to the surface and a second latent reactive activatable group to bond the nanofiber to a biologically active material.

According to still another embodiment, the present invention provides an article having a surface coating including a plurality of nanofibers including one or more natural or synthetic polymeric materials and one or more cross-linking agents each having at least two latent reactive activatable groups. In some embodiments, a biologically active material is bonded to the nanofibers.

According to yet still another embodiment, the present invention is a cell culture plate including a surface coating having at least one nanofiber including one or more polymeric materials and one or more cross-linking agents each having at least two latent reactive activatable groups.

While multiple embodiments are disclosed, still other embodiments of the present invention will become apparent to those skilled in the art from the following detailed description, which illustrates and describes exemplary embodiments of the invention. Accordingly, the detailed description is to be regarded as illustrative in nature and not restrictive.

DESCRIPTION OF THE DRAWINGS

FIGS. 1A-1D are electronic images of polycaprolactone nanofibers prepared by the process described in Example 1.

DETAILED DESCRIPTION

Figure 2:
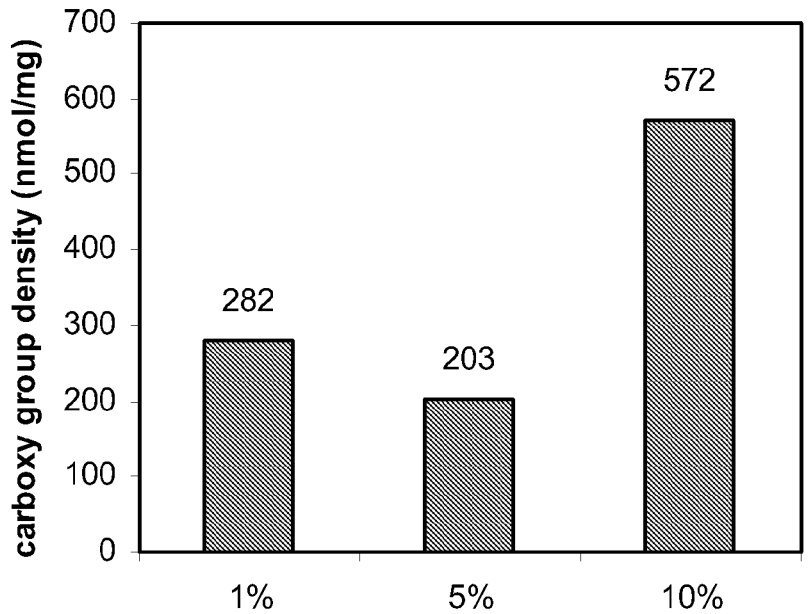
FIGS. 2-4 illustrate functional group densities for nanofibers containing carboxy and amine groups that are described in Example 7.

The present invention is directed toward a latent reactive activatable nanofiber. The latent reactive activatable nanofiber can be used to modify a surface of a substrate to provide a functionalized surface. Biologically active materials may be immobilized on the nanofiber modified surface by reacting with the latent reactive groups exposed on the surface of the substrate. Typically, the biologically active materials retain at least some of their bioactivity after having been immobilized on the nanofiber modified surface.

According to one embodiment of the present invention the nanofiber includes one or more natural or synthetic polymeric materials and cross-linking agents having at least two latent reactive activatable groups. According to a further embodiment of the present invention, the nanofiber may be biodegradable or non-biodegradable and may also include a biologically active material. The latent reactive activatable nanofiber can be used to modify the surface of a substrate by activating at least one of the latent reactive activatable groups to bond the nanofiber to the surface by the formation of a covalent bond between the surface of the substrate and the latent reactive activatable group. The remaining latent reactive activatable group(s) are left accessible on the surface of the substrate, and may be used for further surface modification of the substrate.

A number of processing techniques such as drawing, template synthesis, phase separation, self-assembly or electrospinning have been used to prepare nanofibers. In one embodiment, the nanofiber can be formed by electrospinning a fiber-forming combination that includes one or more polymeric materials and cross-linking agents having at least two latent reactive activatable groups. According to an alternative embodiment of the present invention, the fiber-forming combination may also include biologically active materials. Electrospinning generally involves the introduction of one or more polymeric materials or other fiber-forming solutions or liquid into an electric field, so that the solution or liquid produces nanofibers. When a strong electrostatic field is applied to a fiber-forming combination held in a syringe with a capillary outlet, a pendant droplet of the fiber-forming combination from the capillary outlet is deformed into a Taylor cone. When the voltage surpasses a threshold value, the electric forces overcome the surface tension on the droplet, and a charged jet of the solution or liquid is ejected from the tip of the Taylor cone. The ejected jet then moves toward a collecting metal screen that acts as a counter electrode having a lower electrical potential. The jet is split into small charged fibers or fibrils and any solvent present evaporates leaving behind a nonwoven mat formed on the screen.

Electrostatically spun fibers can be produced having very thin diameters. Parameters that influence the diameter, consistency, and uniformity of the electrospun fibers include the polymeric material and cross-linker concentration (loading) in the fiber-forming combination, the applied voltage, and needle collector distance. According to one embodiment of the present invention, a nanofiber has a diameter ranging from about 1 nm to about 100 µm. In other embodiments, the nanofiber has a diameter in a range of about 1 nm to about 1000 nm. Further, the nanofiber may have an aspect ratio in a range of at least about 10 to about at least 100. It will be appreciated that, because of the very small diameter of the fibers, the fibers have a high surface area per unit of mass. This high surface area to mass ratio permits fiber-forming solutions or liquids to be transformed from liquid or solvated fiber-forming materials to solid nanofibers in fractions of a second.

The polymeric material used to form the nanofiber may be selected from any fiber forming material which is compatible with the cross-linking agents. Depending upon the intended application, the fiber-forming polymeric material may be hydrophilic, hydrophobic or amphiphilic. Additionally, the fiber-forming polymeric material may be a thermally responsive polymeric material.

Synthetic or natural, biodegradable or non-biodegradable polymers may form the nanofiber. A "synthetic polymer" refers to a polymer that is synthetically prepared and that includes non-naturally occurring monomeric units. For example, a synthetic polymer can include non-natural monomeric units such as acrylate or acrylamide units. Synthetic polymers are typically formed by traditional polymerization reactions, such as addition, condensation, or free-radical polymerizations. Synthetic polymers can also include those having natural monomeric units, such as naturally-occurring peptide, nucleotide, and saccharide monomeric units in combination with non-natural monomeric units (for example synthetic peptide, nucleotide, and saccharide derivatives). These types of synthetic polymers can be produced by standard synthetic techniques, such as by solid phase synthesis, or recombinantly, when allowed.

A "natural polymer" refers to a polymer that is either naturally, recombinantly, or synthetically prepared and that consists of naturally occurring monomeric units in the polymeric backbone. In some cases, the natural polymer may be modified, processed, derivatized, or otherwise treated to change the chemical and/or physical properties of the natural polymer. In these instances, the term "natural polymer" will be modified to reflect the change to the natural polymer (for example, a "derivatized natural polymer", or a "deglycosylated natural polymer").

Nanofiber materials, for example, may include both addition polymer and condensation polymer materials such as polyolefin, polyacetal, polyamide, polyester, cellulose ether and ester, polyalkylene sulfide, polyarylene oxide, polysulfone, modified polysulfone polymers and mixtures thereof. Exemplary materials within these generic classes include polyethylene, poly($\epsilon$-caprolactone), poly(lactate), poly(glycolate), polypropylene, poly(vinylchloride), polymethylmethacrylate (and other acrylic resins), polystyrene, and copolymers thereof (including ABA type block copolymers), poly(vinylidene fluoride), poly(vinylidene chloride), polyvinyl alcohol in various degrees of hydrolysis (87% to 99.5%) in crosslinked and non-crosslinked forms. Exemplary addition polymers tend to be glassy (a Tg greater than room temperature). This is the case for polyvinylchloride and polymethylmethacrylate, polystyrene polymer compositions, or alloys or low in crystallinity for polyvinylidene fluoride and polyvinyl alcohol materials.

In some embodiments of the invention the nanofiber material is a polyamide condensation polymer. In more specific embodiments, the polyamide condensation polymer is a nylon polymer. The term "nylon" is a generic name for all long chain synthetic polyamides. Typically, nylon nomenclature includes a series of numbers such as in nylon-6,6 which indicates that the starting materials are a $C_6$ diamine and a $C_6$ diacid (the first digit indicating a $C_6$ diamine and the second digit indicating a $C_6$ dicarboxylic acid compound). Another nylon can be made by the polycondensation of epsilon caprolactam in the presence of a small amount of water. This reaction forms a nylon-6 (made from a cyclic lactam—also known as epsilon-aminocaproic acid) that is a linear polyamide. Further, nylon copolymers are also contemplated. Copolymers can be made by combining various diamine compounds, various diacid compounds and various cyclic lactam structures in a reaction mixture and then forming the nylon with randomly positioned monomeric materials in a polyamide structure. For example, a nylon 6,6-6,10 material is a nylon manufactured from hexamethylene diamine and a $C_6$ and a $C_{10}$ blend of diacids. A nylon 6-6,6-6,10 is a nylon manufactured by copolymerization of epsilon aminocaproic acid, hexamethylene diamine and a blend of a $C_6$ and a $C_{10}$ diacid material.

Block copolymers can also be used as nanofiber materials. In preparing a composition for the preparation of nanofibers, a solvent system can be chosen such that both blocks are soluble in the solvent. One example is an ABA (styrene-EP-styrene) or AB (styrene-EP) polymer in methylene chloride solvent. Examples of such block copolymers are a Kraton™-type of AB and ABA block polymers including styrene/butadiene and styrene/hydrogenated butadiene(ethylene propylene), a Pebax™-type of epsilon-caprolactam/ethylene oxide and a Sympatex™-type of polyester/ethylene oxide and polyurethanes of ethylene oxide and isocyanates.

Addition polymers such as polyvinylidene fluoride, syndiotactic polystyrene, copolymers of vinylidene fluoride and hexafluoropropylene, polyvinyl alcohol, polyvinyl acetate, amorphous addition polymers, such as poly(acrylonitrile) and its copolymers with acrylic acid and methacrylates, polystyrene, poly(vinyl chloride) and its various copolymers, poly(methyl methacrylate) and its various copolymers, can be solution spun with relative ease because they are soluble at low pressures and temperatures. Highly crystalline polymer like polyethylene and polypropylene generally require higher temperature and high pressure solvents if they are to be solution spun.

Nanofibers can also be formed from polymeric compositions comprising two or more polymeric materials in polymer admixture, alloy format, or in a crosslinked chemically bonded structure. Two related polymer materials can be blended to provide the nanofiber with beneficial properties. For example, a high molecular weight polyvinylchloride can be blended with a low molecular weight polyvinylchloride. Similarly, a high molecular weight nylon material can be blended with a low molecular weight nylon material. Further, differing species of a general polymeric genus can be blended. For example, a high molecular weight styrene material can be blended with a low molecular weight, high impact polystyrene. A Nylon-6 material can be blended with a nylon copolymer such as a Nylon-6; 6,6; 6,10 copolymer. Further, a polyvinyl alcohol having a low degree of hydrolysis such as a 87% hydrolyzed polyvinyl alcohol can be blended with a fully or super hydrolyzed polyvinyl alcohol having a degree of hydrolysis between 98 and 99.9% and higher. All of these materials in admixture can be crosslinked using appropriate crosslinking mechanisms. Nylons can be crosslinked using crosslinking agents that are reactive with the nitrogen atom in the amide linkage. Polyvinyl alcohol materials can be crosslinked using hydroxyl reactive materials such as monoaldehydes, such as formaldehyde, ureas, melamine-formaldehyde resin and its analogues, boric acids, and other inorganic compounds, dialdehydes, diacids, urethanes, epoxies, and other known crosslinking agents. Crosslinking reagent reacts and forms covalent bonds between polymer chains to substantially improve molecular weight, chemical resistance, overall strength and resistance to mechanical degradation.

Biodegradable polymers can also be used in the preparation of an article associated with the nanofibrillar structure. Examples of classes of synthetic polymers that have been studied as biodegradable materials include polyesters, polyamides, polyurethanes, polyorthoesters, polycaprolactone (PCL), polyiminocarbonates, aliphatic carbonates, polyphosphazenes, polyanhydrides, and copolymers thereof. Specific examples of biodegradable materials that can be used in connection with, for example, implantable medical devices include polylactide, polyglycolide, polydioxanone, poly(lactide-co-glycolide), poly(glycolide-co-polydioxanone), polyanhydrides, poly(glycolide-co-trimethylene carbonate), and poly(glycolide-co-caprolactone). Blends of these polymers with other biodegradable polymers can also be used.

In some embodiments, the nanofibers are non-biodegradable polymers. Non-biodegradable refers to polymers that are generally not able to be non-enzymatically, hydrolytically or enzymatically degraded. For example, the non-biodegradable polymer is resistant to degradation that may be caused by proteases. Non-biodegradable polymers may include either natural or synthetic polymers.

The inclusion of cross-linking agents within the composition forming the nanofiber, allows the nanofiber to be compatible with a wide range of support surfaces. The cross-linking agents can be used alone or in combination with other materials to provide a desired surface characteristic.

Suitable cross-linking agents include either monomeric (small molecule materials) or polymeric materials having at least two latent reactive activatable groups that are capable of forming covalent bonds with other materials when subjected to a source of energy such as radiation, electrical or thermal energy. In general, latent reactive activatable groups are chemical entities that respond to specific applied external energy or stimuli to generate active species with resultant covalent bonding to an adjacent chemical structure. Latent reactive groups are those groups that retain their covalent bonds under storage conditions but that form covalent bonds with other molecules upon activation by an external energy source. In some embodiments, latent reactive groups form active species such as free radicals. These free radicals may include nitrenes, carbine or excited states of ketones upon absorption of externally applied electric, electrochemical or thermal energy. Various examples of known or commercially available latent reactive groups are reported in U.S. Pat. Nos. 4,973,493; 5,258,041; 5,563,056; 5,637,460; or 6,278,018.

Eight commercially available multifunctional photo-crosslinkers based on trichloromethyl triazine are available either from Aldrich Chemicals, Produits Chimiques Auxiliaires et de Syntheses, (Longjumeau, France), Shin-Nakamara Chemical, Midori Chemicals Co., Ltd. or Panchim S. A. (France). The eight compounds include 2,4,6-tris(trichloromethyl)-1,3,5 triazine, 2-(methyl)-4,6-bis(trichloromethyl)-1,3,5-triazine, 2-(4-methoxynaphthyl)-4,6-bis(trichloromethyl)-1,3,5-triazine, 2-(4-ethoxynaphthyl)-4,6-bis(trichloromethyl)-1,3,5-triazine, 4-(4-carboxylphenyl)-2,6-bis(trichloromethyl)-1,3,5-triazine, 2-(4-methoxyphenyl)-4,6-bis(trichloromethyl)-1,3,5-triazine, 2-(1-ethen-2-2'-furyl)-4,6-bis(trichloromethyl)-1,3,5-triazine and 2-(4-methoxystyryl)-4,6-bis(trichloromethyl)-1,3,5-triazine.

In some embodiments, the latent reactive groups are the same, while in other embodiments the latent reactive groups may be different. For example, the latent reactive groups may be two different groups that are both activated by radiation. In other embodiments one latent reactive group may by activated by radiation while another latent reactive group may be activated by heat. Suitable cross-linking agents include bi-, tri- and multi-functional monomeric and polymeric materials.

Latent reactive groups that are reactive to thermal or heat energy include a variety of reactive moieties and may include known compounds that decompose thermally to form reactive species that will then form covalent bonds. The covalent bonds allow the cross-linking to bind to adjacent materials. Suitable thermally-reactive groups typically have a pair of atoms having a sensitive or labile bond. Heat labile bonds include oxygen-oxygen bonds such as peroxide bonds, nitrogen-oxygen bonds, and nitrogen-nitrogen bonds. Such bonds will react or decompose at temperatures in a range of not more than 80-200° C.

Both thermally generated carbenes and nitrenes undergo a variety of chemical reactions, including carbon bond insertion, migration, hydrogen abstraction, and dimerization. Examples of carbene generators include diazirines and diazocompounds. Examples of nitrene generators include aryl azides, particularly perfluorinated aryl azides, acyl azides, and triazolium ylides. In addition, groups that upon heating form reactive triplet states, such as dioxetanes, or radical anions and radical cations may also be used to form the thermally-reactive group.

In one embodiment the thermally-reactive group of the cross-linking agent includes a peroxide —(O—O)— group. Thermally-reactive peroxide-containing groups include, for example, thermally-reactive diacyl peroxide groups, thermally-reactive peroxydicarbonate groups, thermally-reactive dialkylperoxide groups, thermally-reactive peroxyester groups, thermally-reactive peroxyketal groups, and thermally-reactive dioxetane groups.

Dioxetanes are four-membered cyclic peroxides that react or decompose at lower temperatures compared to standard peroxides due to the ring strain of the molecules. The initial step in the decomposition of dioxetanes is cleavage of the O—O bond, the second step breaks the C—C bond creating one carbonyl in the excited triplet state, and one in an excited singlet state. The excited triplet state carbonyl can extract a hydrogen from an adjacent material, forming two radical species, one on the adjacent material and one on the carbon of the carbonyl with the oxygen and will form a new covalent bond between the thermally reactive dioxetane and the adjacent material.

Representative thermally reactive moieties are reported in US 20060030669 other representative thermal latent reactive groups are reported in U.S. Pat. No. 5,258,041 both of these documents are hereby incorporated by reference.

Latent reactive groups that are reactive to electromagnetic radiation, such as ultraviolet or visible radiation, are typically referred to as photochemical reactive groups.

The use of latent reactive activatable species in the form of latent reactive activatable aryl ketones is useful. Exemplary latent reactive activatable aryl ketones include acetophenone, benzophenone, anthraquinone, anthrone, anthrone-like heterocycles (i.e., heterocyclic analogs of anthrone such as those having N, O, or S in the 10-position), and their substituted (e.g., ring substituted) derivatives. Examples of aryl ketones include heterocyclic derivatives of anthrone, including acridone, xanthone, and thioxanthone, and their ring substituted derivatives. In particular, thioxanthone, and its derivatives, having excitation energies greater than about 360 nm are useful.

The functional groups of such ketones are suitable because they are readily capable of undergoing an activation/inactivation/reactivation cycle. Benzophenone is an exemplary photochemically reactive activatable group, since it is capable of photochemical excitation with the initial formation of an excited singlet state that undergoes intersystem crossing to the triplet state. The excited triplet state can insert into carbon-hydrogen bonds by abstraction of a hydrogen atom (from a support surface, for example), thus creating a radical pair. Subsequent collapse of the radical pair leads to formation of a new carbon-carbon bond. If a reactive bond (e.g., carbon-hydrogen) is not available for bonding, the ultraviolet light-induced excitation of the benzophenone group is reversible and the molecule returns to ground state energy level upon removal of the energy source. Photochemically reactive activatable aryl ketones such as benzophenone and acetophenone are of particular importance inasmuch as these groups are subject to multiple reactivation in water and hence provide increased coating efficiency.

In some embodiments of the invention, photochemically reactive cross-linking agents may be derived from three different types of molecular families. Some families include one or more hydrophilic portions, i.e., a hydroxyl group (that may be protected), amines, alkoxy groups, etc. Other families may include hydrophobic or amphiphilic portion. In one embodiment, the family has the formula:

L-((D-T-C($R^1$)(XP)CHR$^2$GR$^3$C(=O)R$^4$))$_m$.

L is a linking group. D is O, S, SO, $SO_2$, $NR^5$ or $CR^6R^7$. T is (—$CH_2$—)$_x$, (—$CH_2CH_2$—O—)$_x$, (—$CH_2CH_2CH_2$—O—)$_x$ or (—$CH_2CH_2CH_2CH_2$—O—)$_x$. $R^1$ is a hydrogen atom, an alkyl, alkyloxyalkyl, aryl, aryloxyalkyl or aryloxyaryl group. X is O, S, or $NR^8R^9$. P is a hydrogen atom or a protecting group, with the proviso that P is absent when X is $NR^8R^9$. $R^2$ is a hydrogen atom, an alkyl, alkyloxyalkyl, aryl, aryloxyalkyl or aryloxyaryl group. G is O, S, SO, $SO_2$, $NR^{10}$, ($CH_2$)$_t$—O— or C=O. $R^3$ and $R^4$ are each independently an alkyl, aryl, arylalkyl, heteroaryl, or a heteroarylalkyl group or when $R^3$ and $R^4$ are tethered together via (—$CH_2$—)$_q$, (—$CH_2$—)$_r$C=O(—$CH_2$—)$_s$, (—$CH_2$—)$_r$S(—$CH_2$—)$_s$, (—$CH_2$—)$_r$S=O(—$CH_2$—)$_s$, (—$CH_2$—)$_r$S(O)$_2$(—$CH_2$—)$_s$, or (—$CH_2$—)$_r$NR(—$CH_2$—)$_s$. $R^5$ and $R^{19}$ are each independently a hydrogen atom or an alkyl, aryl, or arylalkyl group. $R^6$ and $R^7$ are each independently a hydrogen atom, an alkyl, aryl, arylalkyl, heteroaryl or heteroarylalkyl group. $R^8$ and $R^9$ are each independently a hydrogen atom, an alkyl, aryl, or arylalkyl group, R is a hydrogen atom, an alkyl group or an aryl group, q is an integer from 1 to about 7, r is an integer from 0 to about 3, s is an integer from 0 to about 3, m is an integer from 2 to about 10, t is an integer from 1 to about 10 and x is an integer from 1 to about 500.

In one embodiment, L is a branched or unbranched alkyl chain having between about 2 and about 10 carbon atoms.

In another embodiment, D is an oxygen atom (O).

In still another embodiment, T is (—$CH_2$—)$_x$ or (—$CH_2CH_2$—O—)$_x$ and x is 1 or 2.

In still yet another embodiment, $R^1$ is a hydrogen atom.

In yet another embodiment, X is an oxygen atom, O, and P is a hydrogen atom.

In another embodiment, $R^2$ is a hydrogen atom.

In still another embodiment, G is an oxygen atom, O.

In still yet another embodiment, $R^3$ and $R^4$ are each individually aryl groups, which can be further substituted, and m is 3.

In one particular embodiment, L is

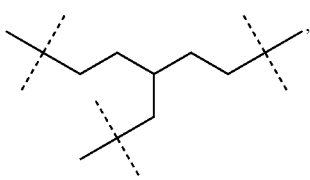

D is O, T is (—$CH_2$—)$_x$, $R^1$ is a hydrogen atom, X is O, P is a hydrogen atom, $R^2$ is a hydrogen atom, G is O, $R^3$ and $R^4$ are phenyl groups, m is 3 and x is 1.

In yet another particular embodiment, L is (—$CH_2$—)$_y$, D is O, T is (—$CH_2$—)$_x$, $R^1$ is a hydrogen atom, X is O, P is a hydrogen atom, $R^2$ is a hydrogen atom, G is O, $R^3$ and $R^4$ are phenyl groups, m is 2, x is 1 and y is an integer from 2 to about 6, and in particular, y is 2, 4 or 6.

In certain embodiments, x is an integer from about 1 to about 500, more particularly from about 1 to about 400, from about 1 to about 250, from about 1 to about 200, from about 1 to about 150, from about 1 to about 100, from about 1 to about 50, from about 1 to about 25 or from about 1 to about 10.

In another embodiment, the family has the formula:

L((T-C($R^1$)(XP)CHR$^2$GR$^3$C(=O)R$^4$))$_m$, and L, T, $R^1$, X, P, $R^2$, G, $R^3$, $R^4$, $R^8$, $R^9$, $R^{19}$, R, q, r, s, m, t and x are as defined above.

In one embodiment, L has a formula according to structure (I):

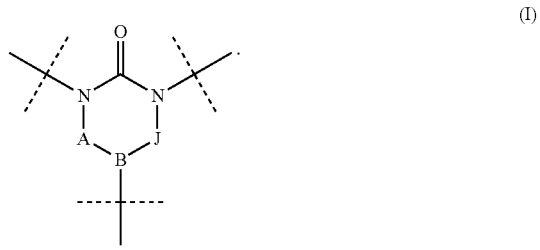

A and J are each independently a hydrogen atom, an alkyl group, an aryl group, or together with B form a cyclic ring, provided when A and J are each independently a hydrogen atom, an alkyl group, or an aryl group then B is not present, B is $NR^{11}$, O, or (—$CH_2$—)$_z$, provided when A, B and J form a ring, then A and J are (—$CH_2$—)$_z$ or C=O, $R^{11}$ is a hydrogen atom, an alkyl group, an aryl group or denotes a bond with T, each z independently is an integer from 0 to 3 and provided when either A or J is C=O, then B is $NR^{11}$, O, or (—$CH_2$—)$_z$ and z must be at least 1.

In another embodiment, T is —$CH_2$—.

In another embodiment, the family has the formula: L-((GTZR$^3$C(=O)R$^4$))$_m$, and L, T, G, $R^3$, $R^4$, $R^{10}$, R, q, r, s, m, t and x are as defined above. Z can be a C=O, COO or CONH when T is (—$CH_2$—)$_x$.

In one embodiment, L has a formula according to structure (I):

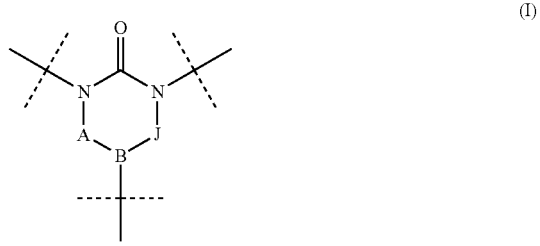

and A, B, J, $R^{11}$, and z are as defined above.

In another embodiment, L has a formula according to structure (II):

$R^{12}, R^{13}, R^{14}, R^{15}, R^{16}, R^{17}$ are each independently a hydrogen atom, an alkyl or aryl group or denotes a bond with T, provided at least two of $R^{12}, R^{13}, R^{14}, R^{15}, R^{16}, R^{17}$ are bonded with T and each K, independently is CH or N.

In another embodiment, the family has the formula:

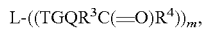

L, G, $R^3$, $R^4$, $R^{10}$, R, q, r, s, m, t and x are as defined above. T is $(-CH_2-)_x$, $(-CH_2CH_2-O-)_x$, $(-CH_2CH_2CH_2-O-)_x$, $(-CH_2CH_2CH_2CH_2-O-)_x$ or forms a bond. Q is $(-CH_2-)_p$, $(-CH_2CH_2-O-)_p$, $(-CH_2CH_2CH_2-O-)_p$ or $(-CH_2CH_2CH_2CH_2-O-)_p$ and p is an integer from 1 to about 10.

In one embodiment, L has a formula according to structure (I):

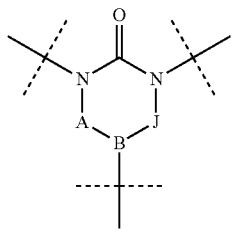

A, B, J, $R^{11}$, and z are as defined above.

In another embodiment, L has a formula according to structure (II):

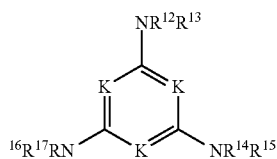

$R^{12}, R^{13}, R^{14}, R^{15}, R^{16}, R^{17}$ are each independently a hydrogen atom, an alkyl or aryl group or denotes a bond with T, provided at least two of $R^{12}, R^{13}, R^{14}, R^{15}, R^{16}, R^{17}$ are bonded with T and each K, independently is CH or N.

In still yet another embodiment, compounds of the present invention provide that $R^3$ and $R^4$ are both phenyl groups and are tethered together via a CO, a S or a $CH_2$.

In yet another embodiment, compounds of the present invention provide when $R^3$ and $R^4$ are phenyl groups, the phenyl groups can each independently be substituted with at least one alkyloxyalkyl group, such as $CH_3O-(CH_2CH_2O-)_n-$, or $CH_3O(-CH_2CH_2CH_2O-)_n-$ a hydroxylated alkoxy group, such as $HO-CH_2CH_2O-$, $HO(-CH_2CH_2O-)_n-$ or $HO(-CH_2CH_2CH_2O-)_n-$, etc. wherein n is an integer from 1 to about 10.

In another embodiment the family has the formula:

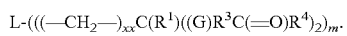

L, each R, $R^1$, each G, each $R^3$, each $R^4$, each $R^{10}$, each q, each r, each s, each t and m are as defined above and xx is an integer from 1 to about 10.

In one embodiment, L has a formula according to structure (I):

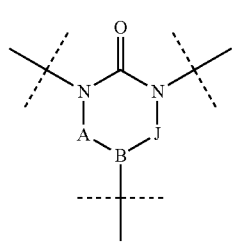

A, B, J, $R^{11}$, and z are as defined above.

In another embodiment, A and B are both hydrogen atoms.

In still another embodiment, xx is 1.

In yet another embodiment, $R^1$ is H.

In still yet another embodiment, G is $(-CH_2-)_tO-$ and t is 1.

In another embodiment, $R^3$ and $R^4$ are each individually aryl groups.

In still yet another embodiment, xx is 1, $R^1$ is H, each G is $(-CH_2-)_tO-$, t is 1 and each of $R^3$ and $R^4$ are each individually aryl groups.

In another embodiment of the invention, the family has the formula:

L, R, $R^1$, $R^2$, $R^3$, $R^4$, $R^8$, $R^9$, $R^{10}$, X, P, G, q, r, s, t, and m are as defined above.

In one embodiment, L is

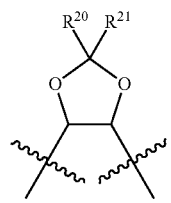

and $R^{20}$ and $R^{21}$ are each individually a hydrogen atom, an alkyl group or an aryl group.

In another embodiment, $R^1$ is H.

In still another embodiment, X is O.

In yet another embodiment, P is H.

In still yet another embodiment, $R^2$ is H.

In another embodiment, G is $(-CH_2-)_tO-$ and t is 1.

In still another embodiment, $R^3$ and $R^4$ are each individually aryl groups.

In yet another embodiment, $R^1$ is H, X is O, P is H, $R^2$ is H, G is $(-CH_2-)_tO-$, t is 1, $R^3$ and $R^4$ are each individually aryl groups and $R^{20}$ and $R^{21}$ are both methyl groups.

In yet another embodiment, the present invention provides a family of compounds having the formula:

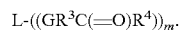

L, G, R, $R^3$, $R^4$, $R^{10}$, q, r, s, m and t are as defined above.

In one embodiment, L is

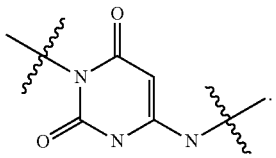 [SMILES: *Nc1cc(=O)n(*)c(=O)[nH]1]

In another embodiment, G is C=O.

In still another embodiment, $R^3$ and $R^4$ are each individually aryl groups.

In yet another embodiment, G is C=O and $R^3$ and $R^4$ are each individually aryl groups.

In yet another embodiment, the present invention provides a family of compounds having the formula:

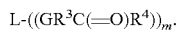

L is a linking group; G is O, S, SO, $SO_2$, $NR^{10}$, $(CH_2)_t$—O— or C=O; $R^3$ and $R^4$ are each independently an alkyl, aryl, arylalkyl, heteroaryl, or an heteroarylalkyl group or when $R^3$ and $R^4$ are tethered together via $(-CH_2-)_q$, $(-CH_2-)_rC=O(-CH_2-)_s$, $(-CH_2-)_rS(-CH_2-)_s$, $(-CH_2-)_rS=O(-CH_2-)_s$, or $(-CH_2-)_rS(O)_2(-CH_2-)_s$, $(-CH_2-)_rNR(-CH_2-)_s$; $R^{10}$ is a hydrogen atom or an alkyl, aryl, or an arylalkyl group; R is a hydrogen atom, an alkyl or an aryl group; q is an integer from 1 to about 7; r is an integer from 0 to about 3; s is an integer from 0 to about 3; m is an integer from 2 to about 10; and t is an integer from 1 to about 10.

"Alkyl" by itself or as part of another substituent refers to a saturated or unsaturated branched, straight-chain or cyclic monovalent hydrocarbon radical having the stated number of carbon atoms (i.e., $C_1$-$C_6$ means one to six carbon atoms) that is derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl, cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. Where specific levels of saturation are intended, the nomenclature "alkanyl," "alkenyl" and/or "alkynyl" is used, as defined below. "Lower alkyl" refers to alkyl groups having from 1 to 6 carbon atoms.

"Alkanyl" by itself or as part of another substituent refers to a saturated branched, straight-chain or cyclic alkyl derived by the removal of one hydrogen atom from a single carbon atom of a parent alkane. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

"Alkenyl" by itself or as part of another substituent refers to an unsaturated branched, straight-chain or cyclic alkyl having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl, prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkyloxyalkyl" refers to a moiety having two alkyl groups tethered together via an oxygen bond. Suitable alkyloxyalkyl groups include polyoxyalkylenes, such as polyethyleneoxides, polypropyleneoxides, etc. that are terminated with an alkyl group, such as a methyl group. A general formula for such compounds can be depicted as R'—(OR")$_n$ or (R'O)$_n$—R" wherein n is an integer from 1 to about 10, and R' and R" are alkyl or alkylene groups.

"Alkynyl" by itself or as part of another substituent refers to an unsaturated branched, straight-chain or cyclic alkyl having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Alkyldiyl" by itself or as part of another substituent refers to a saturated or unsaturated, branched, straight-chain or cyclic divalent hydrocarbon group having the stated number of carbon atoms (i.e., $C_1$-$C_6$ means from one to six carbon atoms) derived by the removal of one hydrogen atom from each of two different carbon atoms of a parent alkane, alkene or alkyne, or by the removal of two hydrogen atoms from a single carbon atom of a parent alkane, alkene or alkyne. The two monovalent radical centers or each valency of the divalent radical center can form bonds with the same or different atoms. Typical alkyldiyl groups include, but are not limited to, methandiyl; ethyldiyls such as ethan-1,1-diyl, ethan-1,2-diyl, ethen-1,1-diyl, ethen-1,2-diyl; propyldiyls such as propan-1,1-diyl, propan-1,2-diyl, propan-2,2-diyl, propan-1,3-diyl, cyclopropan-1,1-diyl, cyclopropan-1,2-diyl, prop-1-en-1,1-diyl, prop-1-en-1,2-diyl, prop-2-en-1,2-diyl, prop-1-en-1,3-diyl, cycloprop-1-en-1,2-diyl, cycloprop-2-en-1,2-diyl, cycloprop-2-en-1,1-diyl, prop-1-yn-1,3-diyl, etc.; butyldiyls such as, butan-1,1-diyl, butan-1,2-diyl, butan-1,3-diyl, butan-1,4-diyl, butan-2,2-diyl, 2-methyl-propan-1,1-diyl, 2-methyl-propan-1,2-diyl, cyclobutan-1,1-diyl; cyclobutan-1,2-diyl, cyclobutan-1,3-diyl, but-1-en-1,1-diyl, but-1-en-1,2-diyl, but-1-en-1,3-diyl, but-1-en-1,4-diyl, 2-methyl-prop-1-en-1,1-diyl, 2-methanylidene-propan-1,1-diyl, buta-1,3-dien-1,1-diyl, buta-1,3-dien-1,2-diyl, buta-1,3-dien-1,3-diyl, buta-1,3-dien-1,4-diyl, cyclobut-1-en-1,2-diyl, cyclobut-1-en-1,3-diyl, cyclobut-2-en-1,2-diyl, cyclobuta-1,3-dien-1,2-diyl, cyclobuta-1,3-dien-1,3-diyl, but-1-yn-1,3-diyl, but-1-yn-1,4-diyl, buta-1,3-diyn-1,4-diyl, etc.; and the like. Where specific levels of saturation are intended, the nomenclature alkanyldiyl, alkenyldiyl and/or alkynyldiyl is used. Where it is specifically intended that the two valencies be on the same carbon atom, the nomenclature "alkylidene" is used. A "lower alkyldiyl" is an alkyldiyl group having from 1 to 6 carbon atoms. In some embodiments the alkyldiyl groups are saturated acyclic alkanyldiyl groups in which the radical centers are at the terminal carbons, e.g., methandiyl (methano); ethan-1,2-diyl (ethano); propan-1,3-diyl (propano); butan-1,4-diyl (butano); and the like (also referred to as alkylenes, defined infra).

"Alkylene" by itself or as part of another substituent refers to a straight-chain saturated or unsaturated alkyldiyl group having two terminal monovalent radical centers derived by the removal of one hydrogen atom from each of the two terminal carbon atoms of straight-chain parent alkane, alkene or alkyne. The location of a double bond or triple bond, if present, in a particular alkylene is indicated in square brackets. Typical alkylene groups include, but are not limited to, methylene (methano); ethylenes such as ethano, etheno, ethyno; propylenes such as propano, prop[1]eno, propa[1,2]dieno, prop[1]yno, etc.; butylenes such as butano, but[1]eno, but[2]eno, buta[1,3]dieno, but[1]yno, but[2]yno, buta[1,3]diyno, etc.; and the like. Where specific levels of saturation are intended, the nomenclature alkano, alkeno and/or alkyno is used. In some embodiments, the alkylene group is ($C_1$-$C_6$) or ($C_1$-$C_3$) alkylene. Other embodiments include straight-chain saturated alkano groups, e.g., methano, ethano, propano, butano, and the like.

"Aryl" by itself or as part of another substituent refers to a monovalent aromatic hydrocarbon group having the stated number of carbon atoms (i.e., $C_5$-$C_{15}$ means from 5 to 15 carbon atoms) derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like, as well as the various hydro isomers thereof. In some embodiments, the aryl group is ($C_5$-$C_{15}$) aryl or, alternatively, ($C_5$-$C_{10}$) aryl. Other embodiments include phenyl and naphthyl.

"Arylalkyl" by itself or as part of another substituent refers to an acyclic alkyl radical in which one of the hydrogen atoms bonded to a carbon atom, typically a terminal or $sp^3$ carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. Preferably, an arylalkyl group is ($C_7$-$C_{30}$) arylalkyl, e.g., the alkanyl, alkenyl or alkynyl moiety of the arylalkyl group is ($C_1$-$C_{10}$) and the aryl moiety is ($C_6$-$C_{20}$), more preferably, an arylalkyl group is ($C_7$-$C_{20}$) arylalkyl, e.g., the alkanyl, alkenyl or alkynyl moiety of the arylalkyl group is ($C_1$-$C_8$) and the aryl moiety is ($C_6$-$C_{12}$).

Aryloxyalkyl" refers to a moiety having an aryl group and an alkyl group tethered together via an oxygen bond. Suitable aryloxyalkyl groups include phenyloxyalkylenes, such as methoxyphenyl, ethoxyphenyl, etc.

"Cycloalkyl" by itself or as part of another substituent refers to a cyclic version of an "alkyl" group. Typical cycloalkyl groups include, but are not limited to, cyclopropyl; cyclobutyls such as cyclobutanyl and cyclobutenyl; cyclopentyls such as cyclopentanyl and cycloalkenyl; cyclohexyls such as cyclohexanyl and cyclohexenyl; and the like.

"Cycloheteroalkyl" by itself or as part of another substituent refers to a saturated or unsaturated cyclic alkyl radical in which one or more carbon atoms (and any associated hydrogen atoms) are independently replaced with the same or different heteroatom. Typical heteroatoms to replace the carbon atom(s) include, but are not limited to, N, P, O, S, Si, etc. Where a specific level of saturation is intended, the nomenclature "cycloheteroalkanyl" or "cycloheteroalkenyl" is used. Typical cycloheteroalkyl groups include, but are not limited to, groups derived from epoxides, imidazolidine, morpholine, piperazine, piperidine, pyrazolidine, pyrrolidine, quinuclidine, and the like.

"Halogen" or "Halo" by themselves or as part of another substituent, unless otherwise stated, refer to fluoro, chloro, bromo and iodo.

"Haloalkyl" by itself or as part of another substituent refers to an alkyl group in which one or more of the hydrogen atoms are replaced with a halogen. Thus, the term "haloalkyl" is meant to include monohaloalkyls, dihaloalkyls, trihaloalkyls, etc. up to perhaloalkyls. For example, the expression "($C_1$-$C_2$) haloalkyl" includes fluoromethyl, difluoromethyl, trifluoromethyl, 1-fluoroethyl, 1,1-difluoroethyl, 1,2-difluoroethyl, 1,1,1-trifluoroethyl, perfluoroethyl, etc.

"Heteroalkyl, Heteroalkanyl, Heteroalkenyl, Heteroalkynyl" by itself or as part of another substituent refer to alkyl, alkanyl, alkenyl and alkynyl radical, respectively, in which one or more of the carbon atoms (and any associated hydrogen atoms) are each independently replaced with the same or different heteroatomic groups. Typical heteroatomic groups include, but are not limited to, —O—, —S—, —O—O—, —S—S—, —O—S—, —NR'—, =N—N=, —N=N—, —N=N—NR'—, —PH—, —P(O)$_2$—, —O—P(O)$_2$—, —S(O)—, —S(O)$_2$—, —SnH$_2$— and the like, where R' is hydrogen, alkyl, substituted alkyl, cycloalkyl, substituted cycloalkyl, aryl or substituted aryl.

"Heteroaryl" by itself or as part of another substituent, refers to a monovalent heteroaromatic radical derived by the removal of one hydrogen atom from a single atom of a parent heteroaromatic ring system. Typical heteroaryl groups include, but are not limited to, groups derived from acridine, arsindole, carbazole, β-carboline, benzoxazine, benzimidazole, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. Preferably, the heteroaryl group is from 5-20 membered heteroaryl, more preferably from 5-10 membered heteroaryl. Suitable heteroaryl groups are those derived from thiophene, pyrrole, benzothiophene, benzofuran, indole, pyridine, quinoline, imidazole, oxazole and pyrazine.

"Heteroarylalkyl" by itself or as part of another substituent refers to an acyclic alkyl group in which one of the hydrogen atoms bonded to a carbon atom, typically a terminal or $sp^3$ carbon atom, is replaced with a heteroaryl group. Where specific alkyl moieties are intended, the nomenclature heteroarylalkanyl, heteroarylakenyl and/or heteroarylalkynyl is used. In some embodiments, the heteroarylalkyl group is a 6-21 membered heteroarylalkyl, e.g., the alkanyl, alkenyl or alkynyl moiety of the heteroarylalkyl is ($C_1$-$C_6$) alkyl and the heteroaryl moiety is a 5-15-membered heteroaryl. In other embodiments, the heteroarylalkyl is a 6-13 membered heteroarylalkyl, e.g., the alkanyl, alkenyl or alkynyl moiety is ($C_1$-$C_3$) alkyl and the heteroaryl moiety is a 5-10 membered heteroaryl.

"Hydroxyalkyl" by itself or as part of another substituent refers to an alkyl group in which one or more of the hydrogen atoms are replaced with a hydroxyl substituent. Thus, the term "hydroxyalkyl" is meant to include monohydroxyalkyls, dihydroxyalkyls, trihydroxyalkyls, etc.

"Parent Aromatic Ring System" refers to an unsaturated cyclic or polycyclic ring system having a conjugated m electron system. Specifically included within the definition of "parent aromatic ring system" are fused ring systems in which one or more of the rings are aromatic and one or more of the rings are saturated or unsaturated, such as, for example, fluorene, indane, indene, phenalene, tetrahydronaphthalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, tetrahydronaphthalene, triphenylene, trinaphthalene, and the like, as well as the various hydro isomers thereof.

"Parent Heteroaromatic Ring System" refers to a parent aromatic ring system in which one or more carbon atoms (and any associated hydrogen atoms) are independently replaced with the same or different heteroatom. Typical heteroatoms to replace the carbon atoms include, but are not limited to, N, P, O, S, Si, etc. Specifically included within the definition of "parent heteroaromatic ring systems" are fused ring systems in which one or more of the rings are aromatic and one or more of the rings are saturated or unsaturated, such as, for example, arsindole, benzodioxan, benzofuran, chromane, chromene, indole, indoline, xanthene, etc. Typical parent heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like.

"Leaving group" is a group that is displaced during a reaction by a nucleophilic reagent. Suitable leaving groups include $S(O)_2Me$, —SMe or halo (e.g., F, Cl, Br, I).

"Linking group" is a group that serves as an intermediate locus between two or more end groups. The nature of the linking group can vary widely, and can include virtually any combination of atoms or groups useful for spacing one molecular moiety from another. For example, the linker may be an acyclic hydrocarbon bridge (e.g., a saturated or unsaturated alkyleno such as methano, ethano, etheno, propano, prop[1]eno, butano, but[1]eno, but[2]eno, buta[1,3]dieno, and the like), a monocyclic or polycyclic hydrocarbon bridge (e.g., [1,2]benzeno, [2,3]naphthaleno, and the like), a simple acyclic heteroatomic or heteroalkyldiyl bridge (e.g., —O—, —S—, —S—O—, —NH—, —PH—, —C(O)—, —C(O)NH—, —S(O)—, —S(O)$_2$—, —S(O)NH—, —S(O)$_2$NH—, —O—CH$_2$—, —CH$_2$—O—CH$_2$—, —O—CH=CH—CH$_2$—, and the like), a monocyclic or polycyclic heteroaryl bridge (e.g., [3,4]furano, pyridino, thiopheno, piperidino, piperazino, pyrazidino, pyrrolidino, and the like) or combinations of such bridges.

"Protecting group" is a group that is appended to, for example, a hydroxyl oxygen in place of a labile hydrogen atom. Suitable hydroxyl protecting group(s) include esters (acetate, ethylacetate), ethers (methyl, ethyl), ethoxylated derivatives (ethylene glycol, propylene glycol) and the like that can be removed under either acidic or basic conditions so that the protecting group is removed and replaced with a hydrogen atom. Guidance for selecting appropriate protecting groups, as well as synthetic strategies for their attachment and removal, may be found, for example, in Greene & Wuts, *Protective Groups in Organic Synthesis,* 3d Edition, John Wiley & Sons, Inc., New York (1999) and the references cited therein (hereinafter "Greene & Wuts").

There are a variety of substrate materials that may be used in the present invention. Plastics such as polyolefins, polystyrenes, poly(methyl)methacrylates, polyacrylonitriles, poly (vinylacetates), poly(vinyl alcohols), chlorine-containing polymeric material such as poly(vinyl)chloride, polyoxymethylenes, polycarbonates, polyamides, polyimides, polyurethanes, phenolics, amino-epoxy resins, polyesters, silicones, cellulose-based plastics, and rubber-like plastics may all be used as supports, providing surfaces that can be modified as described herein. In addition, supports such as those formed of pyrolytic carbon, parylene coated surfaces, and silylated surfaces of glass, ceramic, or metal are suitable for surface modification.

The method of the present invention may involve the attachment or bonding of a biologically active material to a support surface. For example, a nanofiber including a cross-linking agent is provided having two or more latent reactive activatable groups in the presence of a support surface. At least one of the latent reactive activatable groups is activated and covalently bonded to the surface. The remaining latent reactive activatable groups are allowed to revert to their inactive state and are later reactivated in order to later bind a biologically active material in order to attach the biologically active material to the surface of the substrate.

The steps of the method may be performed in any suitable order. For example, a nanofiber including a cross-linking agent, as described herein, can be physically absorbed or adsorbed to a suitable support surface by hydrophobic interactions. Upon activation by a source of energy, at least one of the latent reactive activatable groups (e.g., benzophenone groups) undergoes covalent bond formation at the support surface. With the absence of abstractable hydrogens in the proximity of the remaining unbonded latent reactive activatable group(s), and removal of the source of energy, the latent reactive activatable group returns from an excited state to a ground state. These remaining latent reactive activatable groups are then capable of being reactivated when a biologically active material intended for immobilization is present, and when the treated surface is exposed to another round of illumination. This method can be described as a "two-step" approach, where the latent reactive activatable nanofiber is applied in the first step to create a latent reactive activatable surface, and in the second step, the biologically active material is added for attachment to the activated surface.

Alternatively, the method, described as a "one-step" method, provides that the latent reactive activatable nanofibers of the present invention are combined or mixed together with the biologically active material to form a composition. The resultant composition is used to surface modify materials in a single step of activation by a source of energy. In this case, activation by a source of energy triggers not only covalent bond formation of at least one latent reactive activatable group with the surface of the substrate, but also simultaneously triggers covalent bond formation with any adjacent biologically active materials residing on the surface.

In an alternative embodiment, the nanofiber is formed from a combination or mixture including a polymeric material, a cross-linking agent having at least two latent reactive activatable groups, and a biologically active material. At least one of the latent reactive activatable groups undergoes covalent bond formation at the support surface to bond the nanofiber to the surface of the substrate. The remaining latent reactive activatable group(s) can undergo activation by a source of energy to react with a second biologically active material. Alternatively, the biologically active material incorporated into the nanofiber can itself react with a second biologically active material to provide for further functionalization of the substrate.

In another alternative method, latent reactive activatable nanofibers of the present invention are used to pretreat a substrate surface prior to the application and bonding of molecules that have themselves been functionalized with latent reactive groups. This method is useful in situations where a particularly difficult substrate requires maximal coating durability. In this manner, the number of covalent bonds formed between the substrate surface and the target molecule derivatized with latent reactive groups can typically be increased, as compared to surface modification with a desired latent reactive group-containing target molecule alone.

Suitable biologically active or other target molecules for use in the present invention for attachment to a support surface, encompass a diverse group of substances. Target molecules can be used in either an underivatized form or previously derivatized. Moreover, target molecules can be immobilized singly or in combination with other types of target molecules.

Target molecules can be immobilized to the surface either after (e.g., sequentially) the surface has been primed with the latent reactive activatable nanofibers of the present invention. Alternatively, target molecules are immobilized during (e.g., simultaneously with) attachment of the latent reactive activatable nanofibers to the surface of the substrate.

Typically, target molecules are selected so as to confer particular desired properties to the surface and/or to the device or article bearing the surface. According to one embodiment of the present invention, the target molecule or material is a biologically active material. Biologically active materials which may be immobilized on the surface of the nanofiber modified substrate, or alternatively, provided as a part of the nanofiber composition, generally include, but are not limited to, the following: enzymes, proteins, carbohydrates, nucleic acids, and mixtures thereof. Further examples of suitable target molecules, including biologically active materials, and the surface properties they are typically used to provide, is represented by the following nonlimiting list.

| TARGET MOLECULE | FUNCTIONAL ACTIVITY |
|---|---|
| Synthetic Polymeric Materials | |
| Sulfonic acid-substituted polyacrylamide | Lubricity, negatively charged surface, hydrophilicity |
| Polyacrylamide | Lubricity, protein repulsion, hydrophilicity |
| Polyethylene glycol | Lubricity, cell and protein repulsion, hydrophilicity |
| Polyethyleneimine | Positively charged surface |
| Polylactic acid | Bioerodible surface |
| Polyvinyl alcohol | Lubricity, hydrophilicity |
| Polyvinyl pyrrolidone | Lubricity, hydrophilicity |
| Quaternary amine-substituted polyacrylamide | Lubricity, positively charged surface |
| Silicone | Lubricity, hydrophobicity |
| Conductive polymeric materials, e.g., polyvinylpyridine, polyacetylene, polypyrrole) | Electric conductivity |
| Carbohydrates | |
| Alginic acid | Lubricity, hydrophilicity |
| Cellulose | Lubricity, hydrophilicity, bio-degradable glucose source |

| TARGET MOLECULE | FUNCTIONAL ACTIVITY |
|---|---|
| Chitosan | Positively charged surface, hydrophilicity, hemostatsis |
| Glycogen | Hydrophilicity, biodegradable glucose source |
| Heparin | Antithrombogenicity, hydrophilicity, cell and growth factor attachment, protein affinity |
| Hyaluronic acid | Lubricity, negatively charged surface |
| Pectin | Lubricity, hydrophilicity |
| Mono-, di-saccharides | Hydrophilicity |
| Dextran sulfate | Chromatography media, hydrophilicity |
| Proteins | |
| Antibodies | Antigen binding, immunoassay |
| Antithrombotic agents (e.g. antithrombin III) | Antithrombogenic surface |
| Albumin | Nonthrombogenic surface |
| Attachment proteins/peptides (e.g. collagen) | Cell attachment |
| Enzymes | Catalytic surface |
| Extracellular matrix proteins/peptides | Cell attachment and growth |
| Growth factors, proteins/peptides | Cell growth |
| Hirudin | Antithrombogenic surface |
| Thrombolytic proteins (e.g., streptokinase, plasmin, urokinase) | Thrombolytic activity |
| Lipids | |
| Fatty acids | Hydrophobicity, biocompatibility |
| Mono-, di- and triglycerides | Hydrophobicity, lubricity, bio-degradable fatty acid source |
| Phospholipids | Hydrophobicity, lubricity, bio-degradable fatty acid source |
| Prostaglandins/leukotrienes | Nonthrombogenic surface/immobilized messenger |
| Nucleic Acids | |
| DNA | Substrate for nucleases/affinity binding, genomic assay |
| RNA | Substrate for nucleases/affinity binding, genomic assay |
| Nucleosides, nucleotides | Source of purines, pyrimidines, enzyme cofactor |
| Drugs/Vitamins/Cofactors | |
| Enzyme cofactors | Immobilized enzyme |
| Heme compounds | Globin bindings/surface oxygenation |
| Drugs | Drug activity |
| Nonpolymeric Materials | |
| Dyes (e.g., azo dyestuffs) | Coloring agent |
| Fluorescent compounds (e.g., fluorescein) | Fuorescence |

Target molecules can also be functional polymers. Functional polymers are defined as polymers with functional groups which can be used for further chemical reactions. The functional groups include but are not limited to carboxyl, amine, thiol, epoxy, NHS, aldehyde, azide, phosphine, or hydroxyl.

The latent reactive activatable nanofibers of the present invention can be used in a wide variety of applications including: filters, scaffolds for tissue engineering, protective clothing, reinforcement of composite materials, and sensor technologies.

Medical articles that can be fabricated from or coated or treated with the latent reactive activatable nanofibers of the present invention can include, but are not limited to, the following: catheters including urinary catheters and vascular catheters (e.g., peripheral and central vascular catheters), wound drainage tubes, arterial grafts, soft tissue patches, gloves, shunts, stents, tracheal catheters, wound dressings, sutures, guide wires and prosthetic devices (e.g., heart valves and LVADs). Vascular catheters which can be prepared according to the present invention include, but are not limited to, single and multiple lumen central venous catheters, peripherally inserted central venous catheters, emergency infusion catheters, percutaneous sheath introducer systems, thermodilution catheters, including the hubs and ports of such vascular catheters, leads to electronic devices such as pacemakers, defibrillators, artificial hearts, and implanted biosensors.

Additional articles that can be fabricated from or have a surface that can be coated or treated with the latent reactive activatable nanofibers of the present invention can include, but are not limited to, the following: slides, microtiter wells, microtiter plates, Petri dishes, tissue culture slides, tissue culture plates, tissue culture flasks, cell culture plates, or column supports and/or chromatography media.

In another embodiment, the latent reactive activatable nanofibers of the present invention can be applied to a microscope slide or "chip" for biomolecule immobilization.

In yet another embodiment, the latent reactive activatable nanofibers of the present invention can be applied to a surface of a cell culture plate.

The invention will be further described with reference to the following nonlimiting examples. It will be apparent to those skilled in the art that many changes can be made in the embodiments described without departing from the scope of the present invention. Thus the scope of the present invention should not be limited to the embodiments described in this application, but only by embodiments described by the language of the claims and the equivalents of those embodiments. Unless otherwise indicated, all percentages are by weight.

EXAMPLES

Example 1

Electrospinning Photoreactive Nanofibers

Poly(ε-caprolactone) (PCL), with an average molecular weight of 80 kDa was purchased from Aldrich Chemicals (Milwaukee, Wis.). 0.14 g/ml PCL solution was prepared by dissolving 14 g of PCL in 100 ml of organic solvent mixture (1:1) composed of tetrahydrofuran and N,N-dimethylformamide and mixing it well by vortexing the mixture for 24 h at room temperature. Polymer solutions with 1%, 5%, and 10% weight percent of photocrosslinker content (such as TriLite, tris[2-hydroxy-3-(4-benzoylphenoxy)propyl]isocyanurate) were made by adding different amounts of crosslinker in the PCL solution. The polymer solution was placed in a plastic syringe fitted with a 27 G needle. A syringe pump (KD Scientific, USA) was used to feed the polymer solution into the needle tip. A high voltage power supply (Gamma High Voltage Research, USA) was used to charge the needle tip. The nanofibers were collected onto grounded aluminum foil target located at a certain distance from the needle tip. The fiber meshes were then removed, placed in a vacuum chamber for at least 48 h to remove organic solvent residue, and then stored in a desiccator. The nanofibers were evaluated under microscope. Other photoreactive nanofibers were also prepared by electrospinning TriLite containing polymer solutions. The polymers include nylon 6/6 (Aldrich), polystyrene (Mw 170,000, Aldrich), poly(N-isopropylacrylamide) (PIPAAm, Mw 20,000-25,000, Aldrich), and PEG-PIPAAm. PEG-PIPAAm was synthesized by free radical copolymerization of N-isopropylacrylamide (Aldrich) with poly(ethylene glycol) methyl ether methacrylate (Mw 2,000, Aldrich) in water using ammonium persulfate (Aldrich) as initiator and N,N,N',N'-tetramethylethylenediamine (Aldrich) as catalyst. A photoreactive polymer PVB-BP was synthesized by the reaction of poly(vinyl butyral) (Mw 70,000-100,000, Polysciences) with benzophenone acid chloride which was prepared by the reaction of 4-benzoylbenzoic acid (Aldrich) and oxalyl chloride (Aldrich). Photoreactive PVB-BP nanofibers were prepared by electrospinning PVB-BP solution without TriLite. The electrospinning conditions are summarized in Table 1.

TABLE 1

| Electrospinning Parameters | | | | | |
| --- | --- | --- | --- | --- | --- |
| Polymer | Solvent | Polymer concentration (% w/w) | Applied Voltage (kv) | Feeding Rate (ml/min) | Collection Distance (cm) |
| PCL | THF/DMF | 14 | 20 | 0.3 | 12 |
| Nylon 6/6 | trifluoroethanol | 20 | 17 | 0.1 | 10 |
| Polystyrene | THF/DMF | 14 | 20 | 0.2 | 12 |
| PIPAAm | IPA/DMF | 25 | 16 | 0.2 | 6 |
| PEG-PIPAAm | water | 5 | 12 | 0.2 | 6 |
| PVB-BP | THF/DMF | 25 | 17 | 0.1 | 13 |

The morphology of all the nanofibers was investigated using a Hitachi S-3500N SEM. The fiber samples were mounted on an aluminum stub using carbon tape and gold sputter-coated before viewing. The average diameter of the nanofibers was determined based on the measurements of at least 20 fibers. FIG. 1 shows the typical SEM images of nanofibers with different photocrosslinker concentration. The average fiber diameters of 0%, 1%, 5%, and 10% nanofibers are 208±146 nm, 212±80 nm, 453±146 nm, 315±160 nm, respectively. Highly porous structure was observed in all four formulations of FIG. 1.

Example 2

Acid Derivatized Nanofibers by Polymer Deposition

Poly(acrylic acid) (PAA) was used to provide carboxylic acids on the nanofiber surface. PAA sodium salt with an average molecular weight of 5 kDa was purchased from Aldrich Chemicals. A certain amount of photoreactive PCL nanofiber mesh was immersed in 20 ml 50-100 mg/ml PAA aqueous solution in a quartz round dish (Quartz Scientific, Inc., Fairport Harbor, Ohio). Mild agitation was applied to remove the air bubbles trapped in the nanofibers. UV irradiation was then applied to the mixture in a UVP CL-1000 Ultraviolet Crosslinker (40 watt, 254 nm, distance from light source is 12.7 cm). The nanofiber mesh was flipped over and UV illumination applied again. The coated nanofiber meshes were washed with deionized water for 24 hours and then dried under vacuum to constant weight.

Example 3

Amine Derivatized Nanofibers by Polymer Deposition

Poly(dimethyl acrylamide-co-aminopropyl methacrylamide) (DMA:APMA 80/20) was used to provide amino groups on the surface. The copolymer with an average molecular weight of 5 kDa was synthesized by free-radical copolymerization of DMA and APMA hydrochloride. A certain amount of photoreactive PCL nanofiber mesh was immersed in 20 ml 50 mg/ml PDMA/APMA aqueous solution in a quartz round dish (Quartz Scientific, Inc., Fairport Harbor, Ohio). Mild agitation was applied to remove the air bubbles trapped in the nanofibers. UV irradiation was then applied to the mixture in a UVP CL-1000 Ultraviolet Crosslinker (40 watt, 254 nm, distance from light source is 12.7 cm). The nanofiber mesh was flipped over and UV illumination applied again. The coated nanofiber meshes were washed with deionized water for 24 hours and then dried under vacuum to constant weight.

Example 4

Epoxy Derivatized Nanofibers by Polymer Deposition

Poly(glycidyl methacrylate) (Mw 25,000 Polysciences) was used to provide epoxy groups on the surface. A certain amount of photoreactive PCL nanofiber mesh was immersed in 10 ml 50 mg/ml Poly(glycidyl methacrylate) water/DMSO solution in a quartz round dish (Quartz Scientific, Inc., Fairport Harbor, Ohio). Mild agitation was applied to remove the air bubbles trapped in the nanofibers. UV irradiation was then applied to the mixture in a UVP CL-1000 Ultraviolet Crosslinker (40 watt, 254 nm, distance from light source is 12.7 cm). The nanofiber mesh was flipped over and UV illumination applied again. The coated nanofiber meshes were washed with deionized water for 24 hours and then dried under vacuum to constant weight.

Example 5

Acid Derivatized Nanofibers by Self-Assembly Monolayer (SAM)

SAM acid was used to provide carboxylic acids on the nanofiber surface. SAM acid was synthesized by ISurTec, Inc. A certain amount of photoreactive PCL nanofiber mesh was immersed in 1.0 mg/ml aqueous solution of SAM acid in a quartz round dish (Quartz Scientific, Inc., Fairport Harbor, Ohio). Mild agitation was applied to remove the air bubbles trapped in the nanofibers. UV irradiation was then applied to the mixture in a UVP CL-1000 Ultraviolet Crosslinker (40 watt, 254 nm, distance from light source is 12.7 cm). The nanofiber mesh was flipped over and UV illumination applied again. The coated nanofiber meshes were washed with deionized water for 24 hours and then dried under vacuum to constant weight.

Example 6

Acid Or Amine Derivatized Nanofibers By Graft Polymerization

Preweighed PCL nanofiber meshes were immersed into 20 ml of 50 mg/ml acrylic acid (Aldrich) or 3-aminopropyl methacrylamide (APMA.HCl, Polysciences) aqueous solution in an amber glass bottle. The mixture was bubbled with argon for 2 hrs and transferred to a quartz round dish (Quartz Scientific, Inc., Fairport Harbor, Ohio), followed by 2 min of UV irradiation (Harland Medical UVM400, MN, distance from light source was 8 inches) on each side of the fiber mesh. Thereafter, samples were rinsed with distilled water three times, washed with water overnight and lyophilized.

Example 7

Functionality Characterization

Functional groups (i.e. carboxy and amino) on the nanofibers were measured by reversible ionic dye binding. Calibrations were done with the respective dyes in the solvents used for elution. The fluorescent/UV/vis measurements were performed on a SpectraMax M2 Multi-detection Reader from Molecular Devices.

Carboxy Groups

PCL nanofiber samples were shaken overnight in 10 ml of 10 mg/l thionin (Aldrich Chemicals) in ethanol at room temperature, rinsed three times with ethanol for 30 s each, and then immersed in 10 ml of a solution of 0.01 N HCl in a 1:1 mixture of ethanol and water. After shaking for 1.5 h, fluorescence of the solution was recorded at 620 nm (excitation 485 nm).

Amine Groups

PCL nanofiber samples were shaken overnight in a solution of 50 mmol/L Orange II (Aldrich Chemicals) in water (pH 3, HCl) at room temperature. The samples were washed three times with water (pH 3) and immersed in 10 ml of water (pH 12, NaOH). After shaking for 15 min, the UV/Vis absorption of the solution was recorded at 479 nm.

The functional groups on the nanofiber surface were determined based on 1:1 complexation between functional groups and dye molecules.

Figure 3:
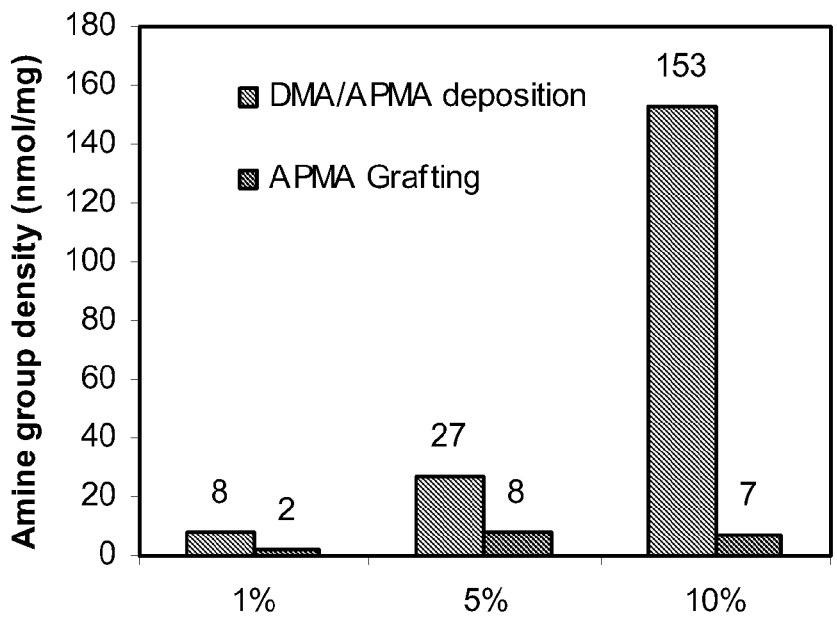
Figure 4:
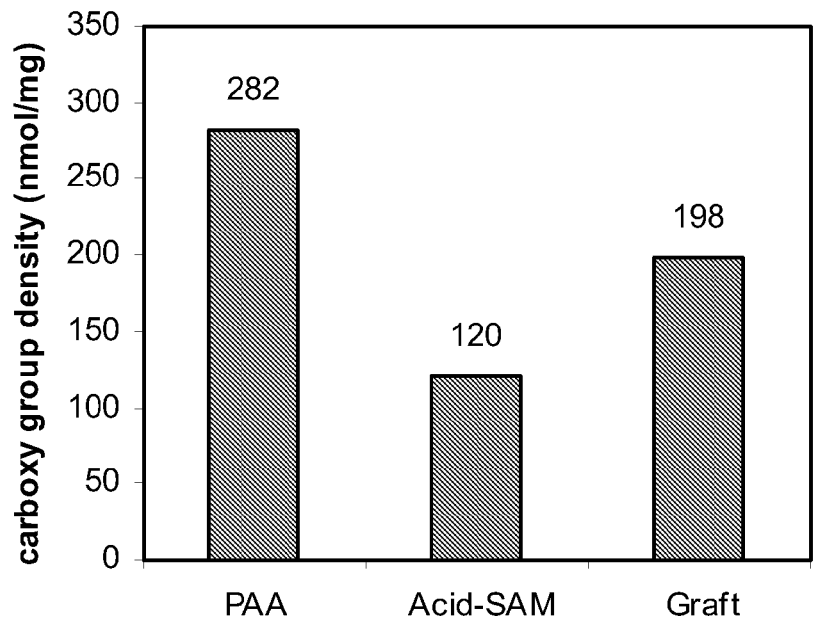

The functional group density was reported as nmol of functional groups per mg of nanofibers (FIGS. 2-4). FIG. 2 shows that PAA deposition on 1%, 5%, and 10% nanofibers yielded carboxy group densities of 282, 203 and 572 nmol/mg, respectively. Theoretically, nanofibers with higher crosslinker content should give higher functional density, given the diameters remain the same. However, the functional group density on 5% nanofibers was slightly lower than that of 1% nanofibers. It should be noted that the same mass of nanofibers with bigger diameter would possess smaller surface area. Therefore, even though 5% nanofibers had more crosslinker in total weight, it might have less accessible photogroups on the fiber surface, leading to a lower density of PAA on the surface. Using the bulk density of PCL (1.12 g/ml) and the diameter of the nanofibers determined by SEM, the density of nmol functional group per mg nanofiber can be converted to number of functional group per $nm^2$ fiber surface. Recalculated functional group densities were 10, 16, and 30 groups/$nm^2$ for 1%, 5% and 10% nanofibers (Table 2), which are all above 0.1 group $nm^2$, the minimum density level we expected. As shown in FIG. 3, the amine density on surfaces created by (80:20) DMA:APMA deposition was lower than carboxy density generated by PAA deposition, which was partially due to 20% amination on DMA:APMA versus 100% carboxylation on PAA. Graft polymerization of APMA to photoreactive nanofibers gave low amine densities (2 nmol/mg, 8 nmol/mg and 7 nmol/mg), indicating poor grafting efficiency, which was probably due to the presence of impurities in the monomer APMA. FIG. 4 shows that all three functionalization methods could generate a high density of carboxy groups on 1% nanofibers with the order of carboxy density from high to low being PAA>AA graft>acid-SAM.

TABLE 2

Carboxy Group Densities and Photogroup Content

| | Diameter (nm) | Carboxy Density (nmol/mg nanofibers) | Carboxy Density (group/nm² fiber surface) |
|---|---|---|---|
| 1% Nanofiber | 212 | 282 | 10 |
| 5% Nanofiber | 453 | 203 | 16 |
| 10% Nanofiber | 315 | 572 | 30 |

Example 8

Porosity Measurement

The porosity of the nanofiber meshes was determined by a liquid displacement method. The mesh sample was immersed in a graduated cylinder containing $V_1$ volume of isopropanol (IPA). A bath sonication is applied to force IPA to enter the pores and get rid of the air bubbles. After 10 min, the volume is recorded as $V_2$. The wetted mesh sample was removed from the cylinder and the residual IPA volume is $V_3$. $(V_1-V_3)$ was the volume of IPA held in the fibers, which represents the volume of porous space in the fibers, whereas $(V_2-V_3)$ was the total volume of filter and porous space. Thus the porosity of the filter was obtained as $(V_1-V_3)/(V_2-V_3)$.

TABLE 3

Porosity of Nanofibers with and without PAA Coating

| | No PAA coating | PAA coated |
|---|---|---|
| 0% TriLite | 89.9% | |
| 1% TriLite | 87% | 89% |
| 5% TriLite | 87.5% | 95.8% |
| 10% TriLite | 90% | 92% |

Example 9

Biomolecule Immobilization

Horse Radish Peroxidase (HRP, PeroxidaseType XII, Sigma) was immobilized on PCL nanofibers through an EDC/NHS coupling method. Carboxy-functionalized nanofiber meshes were immersed in a fresh solution containing 10 mg/ml EDC and 5 mg/ml NHS, in water, adjusted to pH 4.5. After incubation on a shaker (100 rpm) at 4° C. for 30 min, the activated samples were removed, rinsed quickly with ice cold water and immediately immersed in protein solution (5.0 ug/ml, PBS, pH 7.4). After gentle agitation at room temperature for 2 hours, the nanofibers were removed and rinsed with PBS, then washed extensively with PBS-0.1% Triton overnight. The protein immobilized nanofiber was rinsed and analyzed for protein and activity assays.

Example 10

Bicinchoninic Acid (BCA) Protein Assay

The protein loading on the nanofibers including the ones for nonspecific protein adsorption was determined by standard BCA assay. Preweighed protein conjugated nanofibers were dissolved in 2 ml of 1.0 N NaOH containing 2% SDS overnight at 37° C. The solution was then neutralized with 1N HCl and 1 ml of the solution was added to 250 µl 6.1 N TCA solution. After 10 min incubation at 4° C., the sample was centrifuged at 14 k rpm for 5 min to form a protein pellet. The pellet was washed with 200 µl cold acetone twice by centrifugation and dried on a heat block at 95° C. for 5 min. The protein pellet was dissolved in 40 µl of 5% SDS solution in 0.1 N NaOH and 960 µl of distilled water, then used for protein assay using a BCA assay kit (Pierce, Rockford, Ill.). Protein loading level was determined as the weight percentage of immobilized protein per dry weight of nanofibers.

Figure 5:
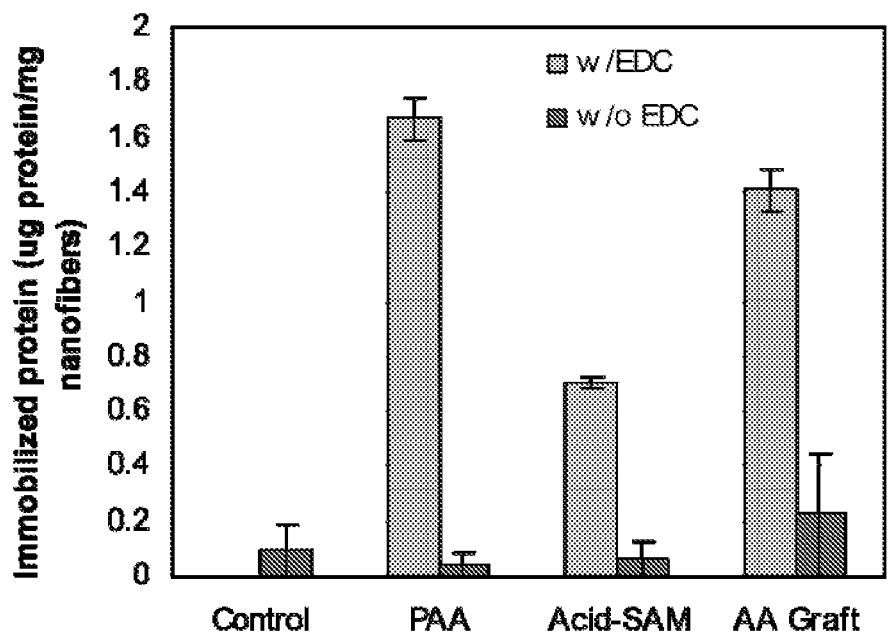
FIG. 5 illustrates protein immobilization levels for nanofibers described in Example 10.

FIG. 5 shows the protein immobilization levels on 1% nanofibers through different surface modifications. BSA was used to construct the calibration curve. PAA modified nanofibers showed the highest protein immobilization (1.7 µg/mg), followed by AA grafted nanofibers (1.4 µg/mg) and acid-SAM coated nanofibers (0.7 µg/mg). The order correlates the order of carboxy density on 1% nanofibers.

Example 11

Bioactivity of Immobilized Protein

The bioactivity of immobilized HRP was determined using a TMB substrate solution. Color development was initiated after 2 ml substrate solution (KPL) was added to HRP conjugated nanofibers. After 10 min, sulfuric acid was added to stop the color development and absorbance at 450 nm was measured. A standard curve of HRP was used to calculate the bioactivity of immobilized HRP.

Figure 6:
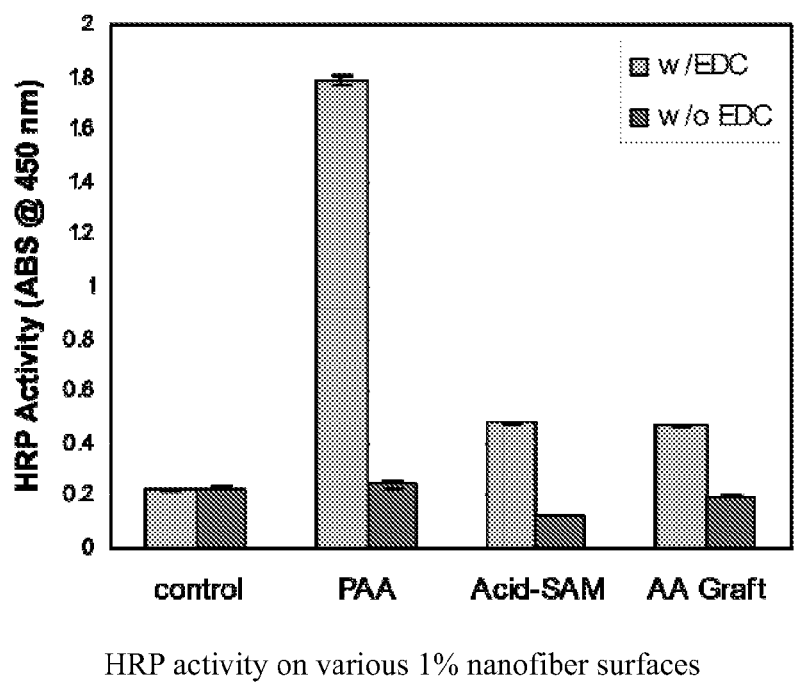
FIG. 6 illustrates horse radish peroxidase activity for nanofibers described in Example 11.

HRP activity was measured by HRP-catalyzed TMB oxidation. As shown in FIG. 6, HRP conjugated on PAA modified nanofibers showed highest activity while lower activity was found on acid-SAM coated and AA grafted nanofibers. Given that the protein level on AA grafted nanofibers was almost twice as much as that of acid-SAM coated nanofibers, the similar activity indicates acid-SAM might be a better spacer candidate for protein conjugation. The activity difference between PAA deposition and AA grafting suggests the orientation of PAA chains on the nanofibers could play an important role in protein activity.

Example 12

Degradation of Photocrosslinked Nanofibers

Degradation was studied in two degradation buffers: 1) PBS, pH 7.4; 2) PBS with 50 U/ml Lipase from *P. cepacia*. The samples for the degradation study were prepared as follows. After electrospinning, the fibers were removed from the aluminum collector by floating them in water to loosen them from the collector and then lyophilized. The fiber meshes were then crosslinked under UV irradiation (UVP CL-1000 Ultraviolet Crosslinker, 40 watt, 254 nm, distance from light source is 5 inches) for 15 min. 40~50 mg of nanofiber was placed into a 15 ml centrifuge tube and 10 ml degradation buffer was added. The tubes were placed on a shaker in a 37° C. incubator. The samples were withdrawn at predetermined time points, washed three times with distilled water by centrifugation and dried to constant weight under vacuum. The experiment was carried out in triplicate. Degradation was calculated as:

% Weight loss=$(M_2-M_1)/M_1 \times 100\%$ where $M_2$ and $M_1$ are the mass of nanofibers after and before degradation.

Figure 7:
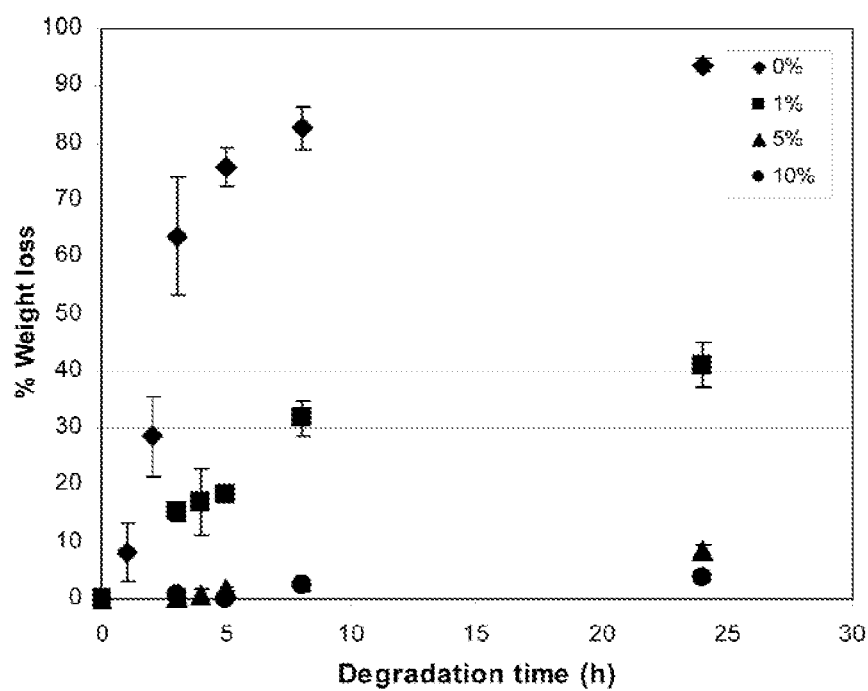
FIG. 7 graphs enzymatic degradation of nanofibers described in Example 12.
Figure 8A:
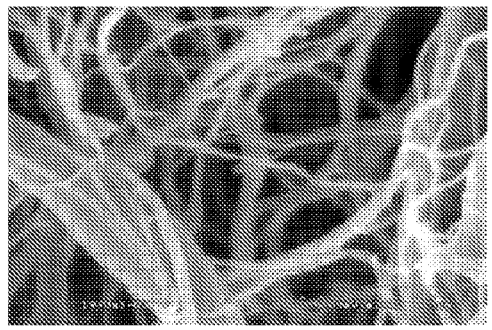
FIGS. 8A-8D are electronic images of enzymatically degraded nanofibers that are described in Example 12.
Figure 8B:
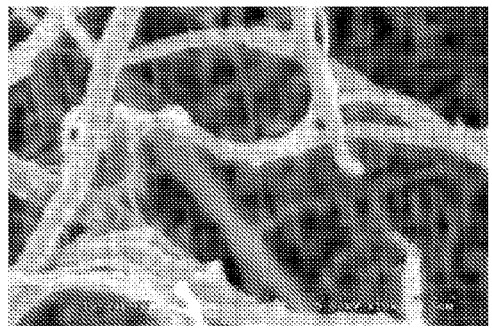
Figure 8C:
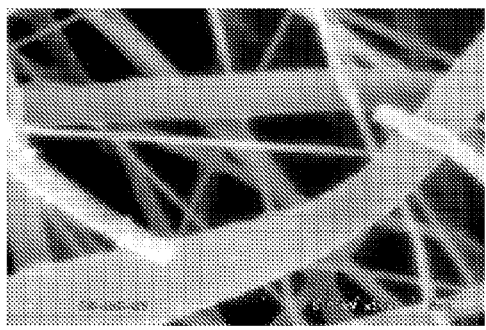
Figure 8D:
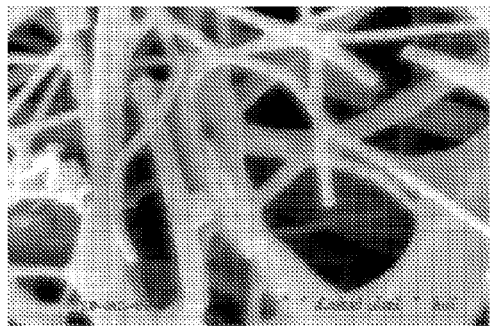

The one important feature of degradable polymers as biomaterials is that they disappear in the body after they have fulfilled their functions and no second surgery is needed to remove them. Different applications require different degradation rates. It is important to understand the degradation behavior of a material and hopefully control it. The degradation is influenced not only by the polymer physicochemical properties such as molecular weight, crystallinity, chain orientation, and other morphological variables, but also by the environmental conditions. Two conditions were investigated in the degradation study: hydrolysis and enzymatic degradation. It is well known that, as a bulk material, the degradation of PCL is very slow due to its high hydrophobicity and high degree of crystallinity. Once PCL is fabricated into nanofibers, it may degrade faster because of a significant increase of surface area. On the other hand, degradation rates may slow down due to crosslinking of PCL by the benzophenone groups. The degradation of PCL nanofibers with four different crosslinker loadings (0%, 1%, 5%, 10% wt/wt) was conducted in phosphate buffered saline PBS (pH 7.4) and PBS containing 50 units/ml Lipase. The results showed that after 23 weeks in PBS, 10.66% weight loss was found for PCL nanofibers with 0% crosslinker, whereas no signs of degradation (less than 4%) showed on nanofibers crosslinked with 1%, 5% and 10% crosslinker. However in the presence of Lipase, the nanofibers degraded much faster with 93.6%, 41.0%, 8.6% and 3.7% weight loss for nanofibers with 0%, 1%, 5% and 10% crosslinker after 24 hrs (FIG. 7). It is concluded that photocrosslinking greatly affects the degradation of nanofibers. The degradation rate slowed down with the increased crosslinker content. It is possible to tune the degradation of nanofibers by changing the photocrosslinker content, which has great promise especially when one material is needed for different applications that require different degradation rates. SEM images showed that after 5 hrs, significant degradation was observed in 0% and 1% nanofibers with fiber surfaces becoming rough, while 5% and 10% nanofibers mostly remained intact with fiber surfaces remaining smooth (FIG. 8).

Example 13

Immobilization of Lysozyme to Photoreactive PCL Nanofibers Using Direct UV Illumination Sixteen nanofiber pieces were cut from larger nanofiber sheets that were electrospun by ISurTec. The nanofiber sheets were prepared using four different TriLite (TL) loadings. The TriLite loadings were: 0%, 1%, 5% and 10%. Eight of the sixteen pieces were prepared for use in a BCA protein assay, while the other eight pieces were prepared for an activity assay. Each of the nanofiber pieces were weighed prior to incubation with lysozyme.

A lysozyme solution was prepared using lysozyme from chicken egg white (Amresco, Solon, Ohio.) The lysozyme was prepared at 50 mg/ml in $dH_2O$. The nanofibers were incubated in the lysozyme solution for one hour at room temperature with shaking.

After the one hour incubation in the lysozyme solution, the nanofibers were removed from the lysozyme solution and placed on a piece of Teflon for the UV illumination. The fibers were illuminated for a total of two minutes (30 seconds per side ×2).

After UV illumination, the nanofibers were placed into new scintillation vials and washed overnight with two ml of PBS/0.1% Triton (Sigma-Aldrich, Milwaukee, Wis.) to remove any unbound lysozyme. The nanofibers were washed at room temperature on the shaker.

Following the overnight wash in PBS/0.1% Triton, each of the nanofiber pieces were rinsed with $dH_2O$ and placed into new scintillation vials. The nanofiber pieces for the activity assay were used immediately for the assay.

Two ml of a 1N NaOH/2% SDS (Sigma-Aldrich, Milwaukee, Wis.) solution was added to the nanofibers for the BCA protein assay to dissolve them. The nanofibers were incubated with the NaOH/SDS solution overnight at 37° C.

Example 14

Lysozyme Activity

A. Immobilized Lysozyme Activity Assay:

An EnzChek® Lysozyme Assay Kit (Molecular Probes, Euguene, Oreg.) was used to determine the activity level of the immobilized lysozyme on the NFs. All of the reagents used for the assay were prepared according to the kit instructions.

A standard curve was prepared in a 96 well plate according to the kit instructions. 1.5 ml of substrate solution (prepared with kit reagents according to the kit instructions) was added to each of the scintillation vials containing the nanofiber pieces. The standards and nanofiber pieces were incubated with the substrate solution for one hour and 50 minutes at 37° C. (protected from light).

After the incubation with the substrate solution, 100 µl of the supernatant from each nanofiber sample was loaded in triplicate to the 96 well plate containing the standards and fluorescence was measured at 518 nm.

B. BCA Protein Assay:

1) Precipitate Lysozyme Using Trichloroacetic Acid (TCA)

Trichloroacetic acid (Sigma-Aldrich, Milwaukee, Wis.) was used to precipitate the lysozyme from the solutions containing the dissolved nanofibers.

The solutions containing the dissolved nanofibers were adjusted to pH 2 using 1N HCL and then placed into eppendorf tubes. TCA was then added to the solutions (1 volume:4 volumes) and the tubes were placed on ice for 10 minutes.

After the 10 minute incubation on ice, the tubes were spun in the microfuge at 14,000 rpm for 5 minutes. The supernatant was removed, leaving the protein pellet intact.

Two hundred nl of cold acetone was then added to each tube to wash the pellet. The tubes were spun again at 14,000 rpm for 5 minutes and the supernatant was removed. This acetone wash was repeated twice for a total of three acetone washes.

After the final acetone wash, the protein pellets were dried for 10 minutes in a heat block to remove any residual acetone.

2) Prepare Protein Samples for BCA Assay

After drying the protein pellets, forty µl of a 0.2N NaOH/ 5% SDS solution was added to each tube to dissolve the pellets. 960 µl of $dH_2O$ was then added to each tube to bring the total volume to 1 ml. The protein solutions were transferred to glass test tubes for the assay.

3) Prepare Lysozyme Standard Curve

A standard curve was prepared using lysozyme (Amresco, Solon, Ohio) in dH$_2$O. Ten standards were prepared in glass test tubes ranging in concentration from 10 μg/ml to 0.0195 μg/ml (1 ml total volume per standard.)

4) Incubate Standards And Experimental Samples With BCA Working Reagent

A QuantiPro™ BCA Assay Kit (Sigma-Aldrich, Milwaukee, Wis.) was used for the assay. One ml of BCA working reagent (prepared according to kit instructions) was added to each of the standards and experimental samples (2 ml total volume per tube). The standards and samples were then incubated at 37° C. for three hours. Two hundred μl of the standard and experimental solutions was loaded in triplicate to a 96 well plate and absorbance was measured at 562 nm.

The results confirmed that a significant amount of lysozyme was conjugated onto PCL nanofibers by direct UV illumination, however, the immobilized lysozyme showed limited activity, indicating the loss of activity during direct UV conjugation.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A latent reactive nanofiber comprising a combination of: (i) a cross-linking agent having at least two latent photochemically reactive groups, and (ii) a fiber forming polymeric material that is compatible with the cross-linking agent, wherein the cross-linking agent is included throughout the latent reactive nanofiber, and wherein the cross-linking agent is tris[2-hydroxy-3-(4-benzoylphenoxy)propyl]isocyanurate having formula:

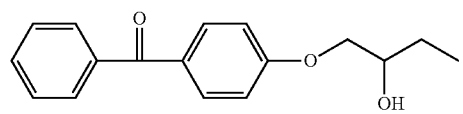

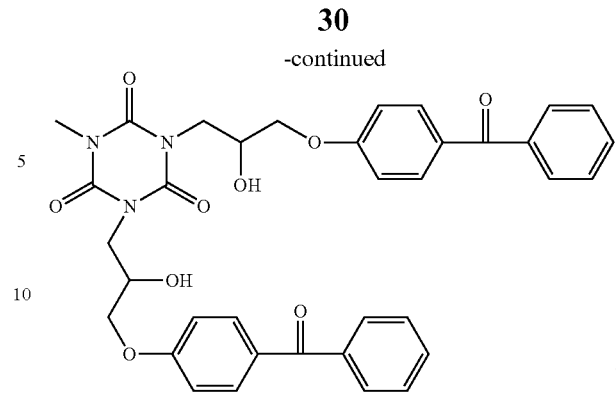

2. The nanofiber according to claim 1 wherein the fiber forming material is a synthetic or natural polymer.

3. The nanofiber according to claim 2 wherein the fiber forming material is a biodegradable polymer selected from polyesters, polyamides, polyurethanes, polyorthoesters, polycaprolactone, polyiminocarbonates, aliphatic carbonates, polyphosphazenes, polyanhydrides, and copolymers of these.

4. The nanofiber according to claim 2 wherein the fiber forming material comprises a polymer having peptide, nucleotide or saccharide monomeric units.

5. The nanofiber according to claim 1 wherein the fiber forming material is a thermally responsive polymeric material.

6. The nanofiber according to claim 5 wherein the thermally responsive polymeric material comprises poly(N-isopropylacrylamide) or polyethylene glycol-poly(N-isopropylacrylamide).

7. The nanofiber according to claim 1 wherein the fiber forming material comprises two or more polymeric materials.

8. The nanofiber according to claim 1 wherein the nanofiber further comprises a biologically active material or a functional polymer.

9. The nanofiber according to claim 1 wherein the cross-linking agent is a tri-functional monomeric or polymeric material.

10. The latent reactive nanofiber according to claim 1, wherein the nanofiber is crosslinked.

11. An article having a surface coating comprising a plurality of latent reactive nanofibers, wherein at least some of the nanofibers comprise a combination of a cross-linking agent having at least two latent photochemically reactive groups, and a fiber forming polymeric material that is compatible with the cross-linking agent, wherein the cross-linking agent is included throughout the latent reactive nanofiber, and wherein the cross-linking agent is tris[2-hydroxy-3-(4-benzoylphenoxy)propyl]isocyanurate having formula:

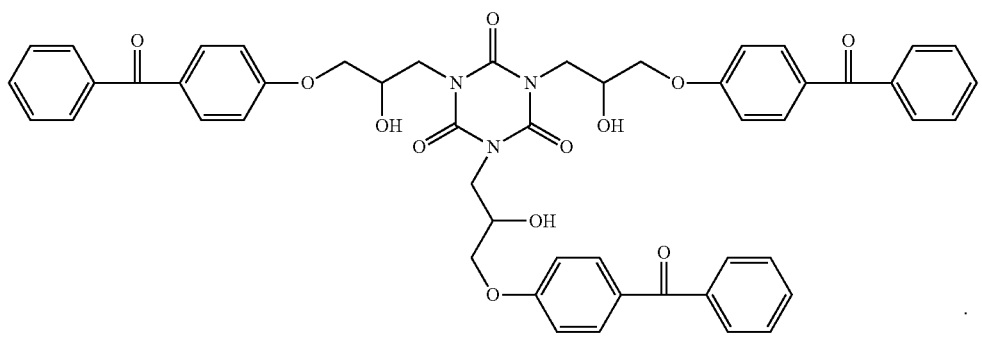 [SMILES: O=C(c1ccccc1)c1ccc(OCC(O)Cn2c(=O)n(CC(O)COc3ccc(C(=O)c4ccccc4)cc3)c(=O)n(CC(O)COc3ccc(C(=O)c4ccccc4)cc3)c2=O)cc1]

12. The article according to claim 11, wherein at least some of the nanofibers comprise a crosslinked combination of a cross-linking agent having at least two latent photochemically reactive groups, and a fiber forming polymeric material that is compatible with the cross-linking agent.

13. The article according to claim 11, wherein at least some of the nanofibers further comprise a biologically active material or a functional polymer.

14. A cell culture article having a surface coating comprising a plurality of latent reactive nanofibers, wherein at least some of the nanofibers comprise a combination of a cross-linking agent having at least two latent photochemically reactive groups, and a fiber forming polymeric material that is compatible with the cross-linking agent, wherein the cross-linking agent is included throughout the latent reactive nanofiber, and wherein the cross-linking agent is tris[2-hydroxy-3-(4-benzoylphenoxy)propyl]isocyanurate having formula:

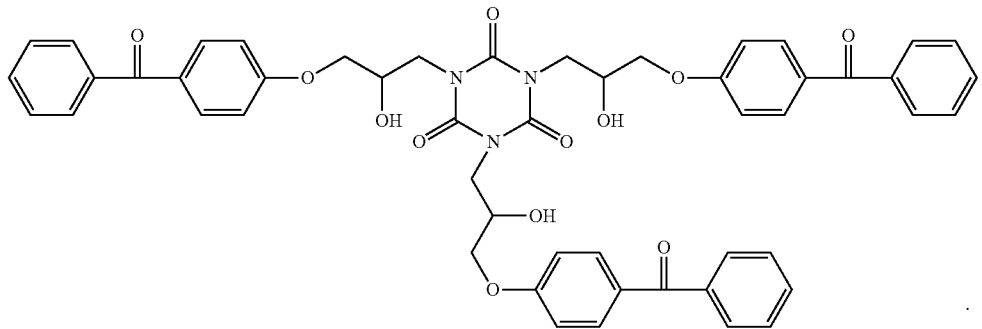 [SMILES: O=C(c1ccccc1)c1ccc(OCC(O)Cn2c(=O)n(CC(O)COc3ccc(C(=O)c4ccccc4)cc3)c(=O)n(CC(O)COc3ccc(C(=O)c4ccccc4)cc3)c2=O)cc1]

15. The cell culture article according to claim 14, wherein at least some of the nanofibers comprise a crosslinked combination of a cross-linking agent having at least two latent photochemically reactive groups, and a fiber forming polymeric material that is compatible with the cross-linking agent.

16. The cell culture article according to claim 14, wherein at least some of the nanofibers further comprise a biologically active material or a functional polymer.

17. The cell culture article according to claim 14, wherein the fiber forming material is a thermally responsive polymeric material.

* * * * *